(12) United States Patent
McCarty et al.

(10) Patent No.: US 8,709,434 B2
(45) Date of Patent: Apr. 29, 2014

(54) COMPOSITIONS FOR INHIBITING NADPH OXIDASE ACTIVITY

(75) Inventors: Mark Fredrick McCarty, San Diego, CA (US); Sheldon Saul Hendler, La Jolla, CA (US); David Michael Rorvik, Vancouver, WA (US); Toyoshi Inoguchi, Fukuoka (JP)

(73) Assignee: PCB Associates, Inc., Las Vegas, NV (US)

( * ) Notice: Subject to any disclaimer, the term of this patent is extended or adjusted under 35 U.S.C. 154(b) by 276 days.

(21) Appl. No.: 12/514,578

(22) PCT Filed: Nov. 13, 2007

(86) PCT No.: PCT/US2007/023887
§ 371 (c)(1),
(2), (4) Date: Mar. 17, 2010

(87) PCT Pub. No.: WO2008/063514
PCT Pub. Date: May 29, 2008

(65) Prior Publication Data
US 2010/0172971 A1    Jul. 8, 2010

Related U.S. Application Data

(60) Provisional application No. 60/858,559, filed on Nov. 13, 2006.

(51) Int. Cl.
*A61K 39/00*    (2006.01)

(52) U.S. Cl.
USPC .................................. 424/185.1; 514/422

(58) Field of Classification Search
None
See application file for complete search history.

(56) References Cited

U.S. PATENT DOCUMENTS

| 5,047,395 | A * | 9/1991 | Wu ............................... 514/15.1 |
| 6,887,260 | B1 | 5/2005 | McDaniel |
| 7,678,889 | B2 * | 3/2010 | Macina et al. ............. 530/387.1 |
| 7,795,397 | B2 * | 9/2010 | Lagarias et al. ............... 530/370 |
| 2006/0083727 | A1 | 4/2006 | Kajander et al. |
| 2010/0021493 | A1 * | 1/2010 | Scoglio et al. ........... 424/195.17 |

FOREIGN PATENT DOCUMENTS

| JP | 58-065216 A1 | 4/1983 |
| JP | 60-013709 A1 | 1/1985 |
| WO | 02/055075 A1 | 7/2002 |

OTHER PUBLICATIONS

Zhou Zhanping, et al., "Effect of Apoprotein on Antioxidant Activity of Phycobiliproteins," Marine Science, Dec. 31, 2003, vol. 27 (5), pp. 77-81. Published by China Academic Journal Electronic Publishing House, China.
Matthew J. Terry, et al., "Inactivation of Phytochrome- and Phycobiliprotein-Chromophore Precursors by Rat Liver Biliverkin Reductase," The Journal of Biological Chemistry, Dec. 15, 1993, vol. 268 (35) pp. 26099-26106.
Lanone Sophie, et al., "Bilirubin decreases NOS2 expression via inhibition of NAD(P)H oxidase: implications for protection against endotoxic shock in rates," FASEB Journel, Aug. 2005, vol. 19 (1), XP002587554, ISSN: 0892-6638.
Riss Jerome, et al., "Phycobiliprotein C-phycocyanin from Spirulina platensis is powerfully responsible for reducing oxidative stress and NADPH oxidase expression induced by an atherogenic diet in hamsters," Journal of Agricultural and Food Chemistry, Sep. 2007, vol. 55( 19): pp. 7962-7967.

* cited by examiner

*Primary Examiner* — Michael G Hartley
*Assistant Examiner* — Robert Cabral
(74) *Attorney, Agent, or Firm* — Lewis Kohn & Fitzwilliam LLP; Donald G. Lewis

(57) ABSTRACT

Phycobilins are disclosed to have prodrug activity as inhibitors of NADPH oxidase activity and are disclosed to be useful in the prophylaxis and/or treatment of medical conditions associated with or linked to an NADPH oxidase activity. Compositions containing phycobilins are described which facilitate the administration of phycobilins.

30 Claims, 4 Drawing Sheets

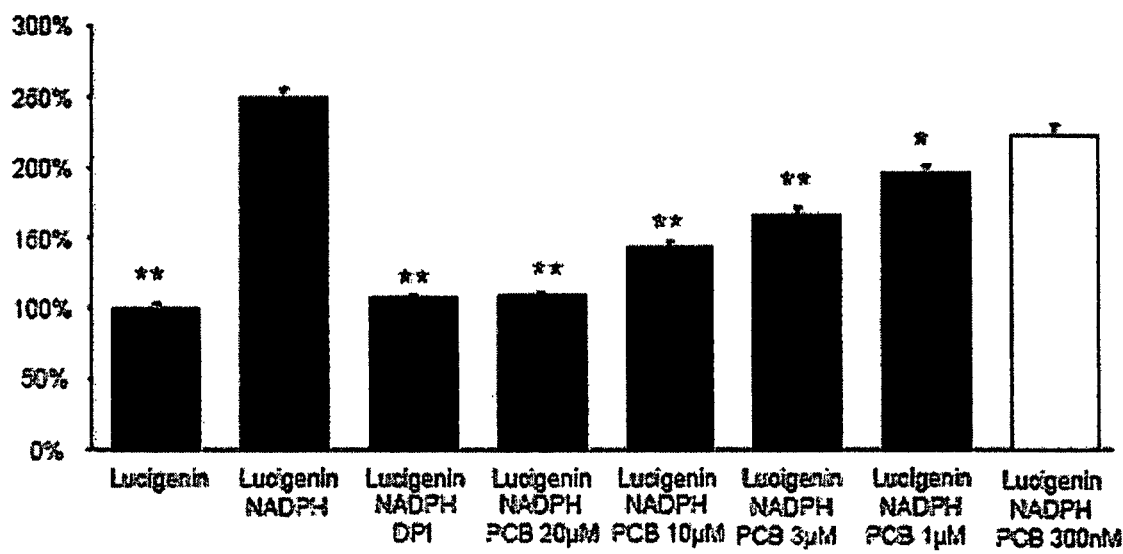
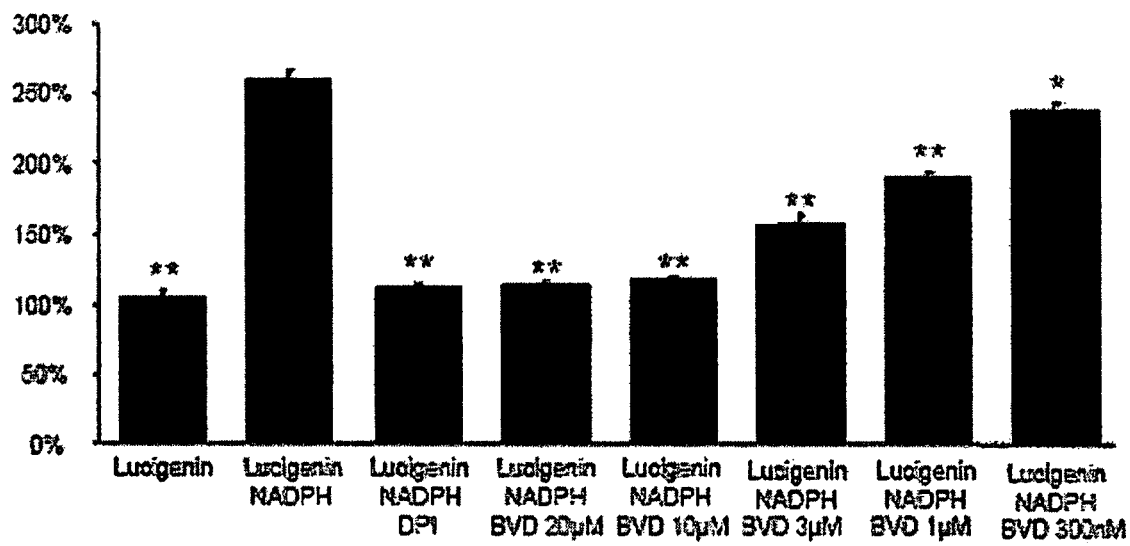
FIGURE 1 A (top panel) and B (bottom panel)

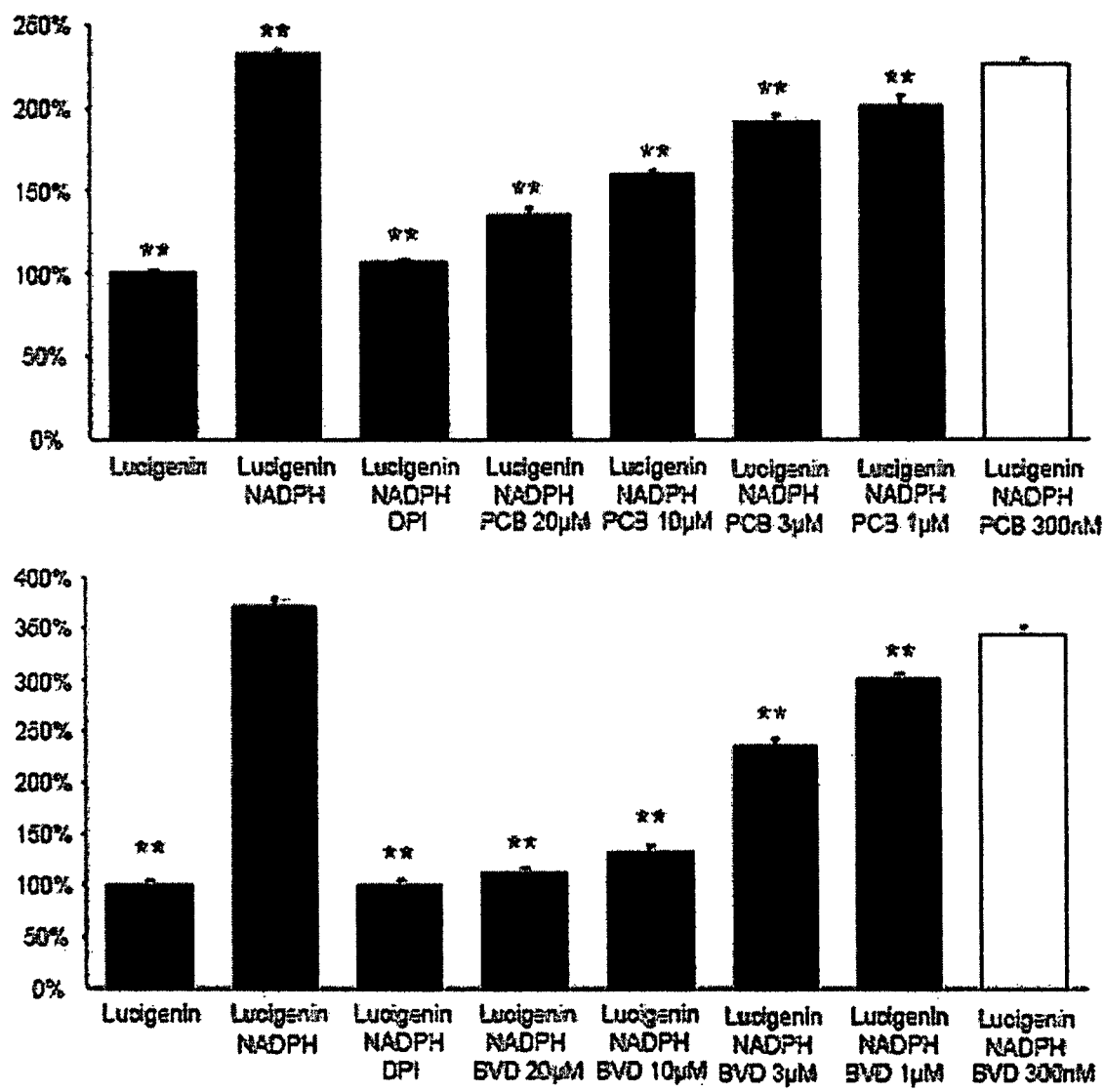
FIGURE 2 A (top panel) and B (bottom panel)

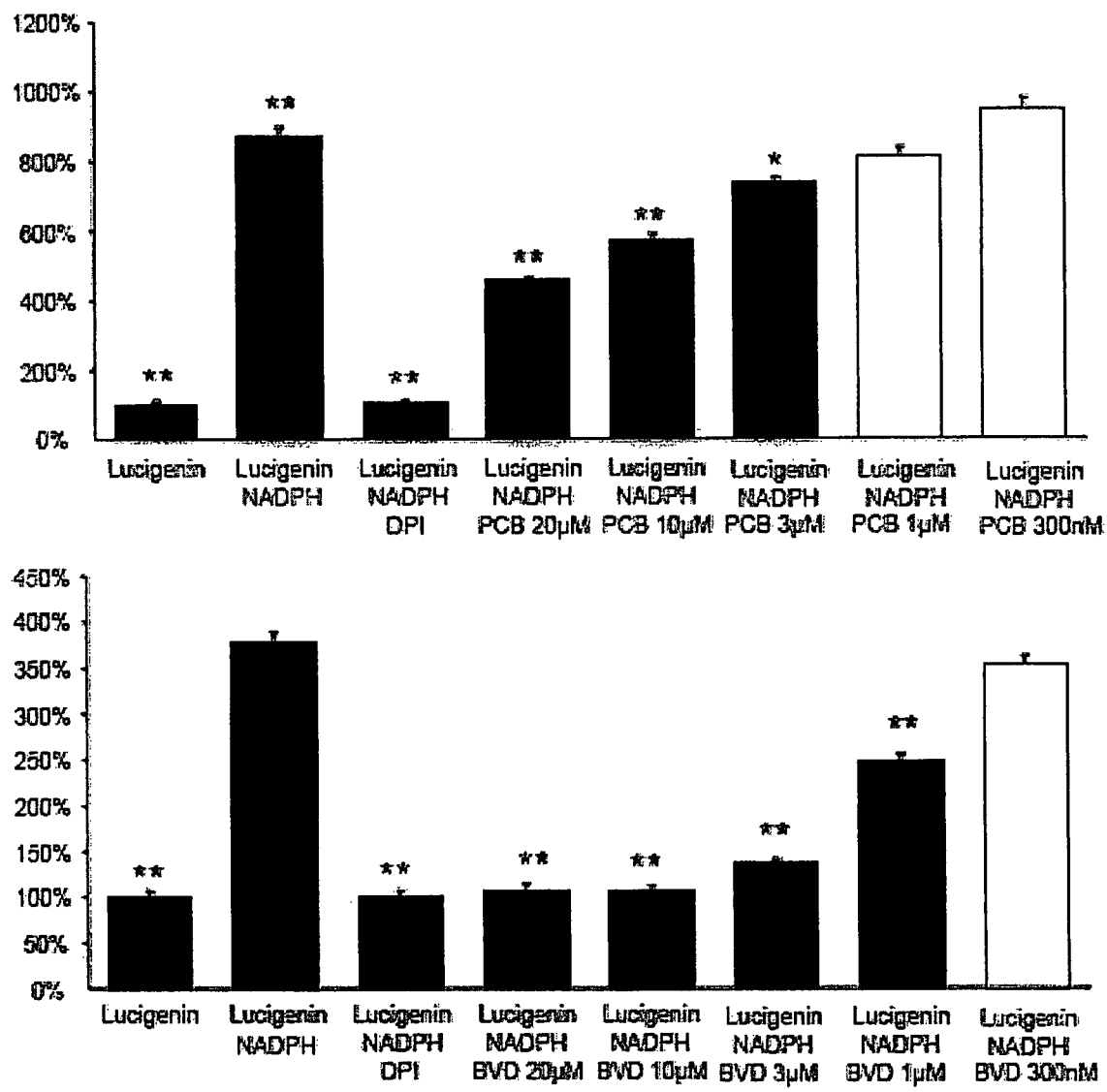
FIGURE 3 A (top panel) and B (bottom panel)

A
B

COMPOSITIONS FOR INHIBITING NADPH OXIDASE ACTIVITY

CROSS REFERENCE TO RELATED APPLICATIONS

This application is a national entry of PCT/US2007/23887, filed on Nov. 13, 2007, which claims benefit of U.S. provisional application 60/858,559, filed on Nov. 13, 2006.

FIELD OF THE INVENTION

The invention relates to compositions and methods for the prophylaxis or treatment of medical conditions associated with or linked to an NADPH oxidase activity. More particularly, the invention relates to compositions and processes which use phycobilins as prodrugs and which convert to phycorubin upon administration to a mammalian subject for inhibiting NADPH oxidase activity.

BACKGROUND

The enzyme NADPH oxidase transfers electrons from NADPH to oxygen, resulting in the generation of reactive oxygen species (ROSs), including $O_2^-$ and $H_2O_2$. NADPH oxidase is expressed in neutrophils where bursts of reactive oxygen species are utilized to kill pathogens. NADPH oxidase expression and activity is also observed in other cells and tissues of the mammalian body, in which it functions as a modulator of intracellular signaling pathways.

Unfortunately, in a high proportion of non-infectious pathologies, NADPH oxidase becomes overexpressed and/or overactivated in affected tissues, and the resulting production of oxidants often either mediates or exacerbates the pathology. Indeed, activated NADPH oxidase appears to be the chief source of excess oxidant stress in most pathological disorders. NADPH oxidase overactivity can stimulate pro-inflammatory mechanisms, promote tissue fibrosis and bone resorption, and, in the vascular system, antagonize the crucial protective activity of nitric oxide. Oxidants produced by NADPH oxidase can also induce structural damage to critical cellular targets, including DNA, and can boost the growth factor activity of cancers. (Meyer J W et al. FEBS Lett 2000; 472:1-4; Zalba G et al. Hypertension 2001; 38:1395-9; Inoguchi T et al. J Am Soc Nephrology 2003; 14:S227-32; Li J M et al. Hypertension 2002; 40:477-84; Bateller R et al. J Clin Invest 2003:112:1383-94; Darden A G et al. J Bone Mineral Res 1996; 11:671-5; Ohshima H et al. Arch Biochem Biophys 2003; 417:3-11; Mander P et al. J Neuroinflammation 2005; 2:20; Brar S S et al. Am J Physiol Cell Physiol 2002; 282: C1212-24; and other citations below.) Thus, there is a widespread consensus among medical scientists that safe strategies for achieving partial inhibition of NADPH oxidase activity could have considerable utility for prevention and/or treatment of a wide range of disorders.

Indeed, it is now believed that the beneficial effects of certain commonly used drugs, including statins and ACE inhibitors, are mediated in part by an indirect suppression of NADPH oxidase activity in certain tissues. However, to date no drug or phytonutrient is currently available for clinical or dietary use that can directly inhibit NADPH oxidase activity in most or all tissues.

Hence, what is needed is an inhibitor of NADPH oxidase that can be readily mass produced, that can be used to inhibit NADPH oxidase activity, and that can be used to prevent or treat conditions associated with NADPH oxidase activity.

SUMMARY

One aspect of the invention is directed to a phycochemical composition for administration to a mammalian subject. The phycochemical composition has a prodrug activity for inhibiting NADPH oxidase activity. The phycochemical composition comprises an isolated phycobilin dissolved or suspended within a pharmaceutically acceptable carrier and a capsule having a gelatinous case for containing said isolated phycobilin. The isolated phycobilin is converted to a phycorubin when administered to said mammalian subject for inhibiting NADPH oxidase activity. In preferred embodiments, the isolated phycobilin is selected from the group consisting of phycocyanobilin, phycoerythrobilin, phytochromobilin, each phycobilin optionally including a peptide fragment of a phycocyanin conjugated thereto. In a further preferred embodiment, the pharmaceutically acceptable carrier is dry and the capsule is optionally a hard gel. In a further preferred embodiment, the pharmaceutically acceptable carrier is liquid and the capsule is optionally soft. In other preferred embodiments, the phycochemical composition further comprise one or more ingredient selected from the group consisting of folic acid, L-arginine, policosanol, soy isoflavone, green tea extract, taurine, coenzyme Q10, potassium salt, magnesium, fish oil, vitamin C, selenium, lutein, zeathanthin, zinc, benfotiamine, and pyridoxamine. This aspect of the invention, viz., capsules containing an isolated phycobilin dissolved or suspended therein within a pharmaceutically acceptable carrier, can be readily manufactured by persons of ordinary skill in the art by adapting known conventional methods within this field in accordance with the description provided herein.

Another aspect of the invention is directed to another phycochemical composition for administration to a mammalian subject. Again, the phycochemical composition has a prodrug activity for inhibiting NADPH oxidase activity. However, in this aspect of the invention, the phycochemical composition comprises an isolated phycobilin admixed with a pharmaceutically acceptable carrier material or a food grade filler and compressed into a tablet. The isolated phycobilin is converted to a phycorubin when administered to the mammalian subject for inhibiting NADPH oxidase activity. In preferred embodiments, the isolated phycobilin is selected from the group consisting of phycocyanobilin, phycoerythrobilin, phytochromobilin, each phycobilin optionally including a peptide fragment of a phycocyanin conjugated thereto. In other preferred embodiments, the phycochemical composition further comprise one or more ingredient selected from the group consisting of folic acid, L-arginine, policosanol, soy isoflavone, green tea extract, taurine, coenzyme Q10, potassium salt, magnesium, fish oil, vitamin C, selenium, lutein, zeathanthin, zinc, benfotiamine, and pyridoxamine. This aspect of the invention, viz., tablets made by compression of an isolated phycobilin admixed with a pharmaceutically acceptable carrier material or a food grade filler, can be readily manufactured by persons of ordinary skill in the art by adapting conventional methods known within this field in accordance with the description provided herein.

Another aspect of the invention is directed to a further phycochemical composition for parenteral administration to a mammalian subject. Again, the phycochemical composition has a prodrug activity for inhibiting NADPH oxidase activity. However, in this aspect of the invention, the phycochemical composition comprises an isolated phycobilin dissolved or suspended within a physiologically acceptable sterile solvent suitable for injection. The isolated phycobilin is converted to a phycorubin when administered to the mammalian subject for inhibiting NADPH oxidase activity. In preferred embodiments, the isolated phycobilin is selected from the group consisting of phycocyanobilin, phycoerythrobilin, phytochromobilin, each phycobilin optionally including a peptide fragment of a phycocyanin conjugated thereto. The physiologically acceptable sterile solvent suitable for injection can be manufactured by conventional means known to persons skilled in the art and described herein. This aspect of the invention, viz., an isolated phycobilin dissolved or suspended within a physiologically acceptable sterile solvent suitable for injection, can be readily manufactured by persons of ordinary skill in the art by adapting conventional methods known within this field in accordance with the description provided herein.

Another aspect of the invention is directed to a phycochemical composition for topical administration to a mammalian subject. Again, in this aspect of the invention, the phycochemical composition has a prodrug activity for inhibiting NADPH oxidase activity. However, the phycochemical composition comprises an isolated phycobilin dissolved or suspended within a dermatologically acceptable emollient carrier. The isolated phycobilin is converted to a phycorubin when topically administered to the mammalian subject for inhibiting NADPH oxidase activity. In preferred embodiments, the isolated phycobilin is selected from the group consisting of phycocyanobilin, phycoerythrobilin, phytochromobilin, each phycobilin optionally including a peptide fragment of a phycocyanin conjugated thereto. In another preferred embodiment, the phycochemical composition serves as a sunscreen. This aspect of the invention, viz., a topical composition made from an isolated phycobilin dissolved or suspended within a dermatologically acceptable emollient carrier, can be readily manufactured by persons of ordinary skill in the art by adapting conventional methods known within this field in accordance with the description provided herein.

Another aspect of the invention is directed to a nutraceutical composition. The neutraceutical composition comprises a nutrient substance admixed with an isolated phycobilin. In a preferred embodiment, the isolated phycobilin is selected from the group consisting of phycocyanobilin, phycoerythrobilin, phytochromobilin, each phycobilin optionally including a peptide fragment of a phycocyanin conjugated thereto. This aspect of the invention, viz., neutraceutical composition having a nutrient substance admixed with an isolated phycobilin, can be readily manufactured by persons of ordinary skill in the art by adapting conventional methods known within this field in accordance with the description provided herein.

Another aspect of the invention is directed to a cosmeceutical composition. The cosmeceutical composition comprises a cosmetic substance admixed with an isolated phycobilin. In a preferred embodiment, the isolated phycobilin is selected from the group consisting of phycocyanobilin, phycoerythrobilin, phytochromobilin, each phycobilin optionally including a peptide fragment of a phycocyanin conjugated thereto. This aspect of the invention, viz., cosmeceutical composition comprises a cosmetic substance admixed with an isolated phycobilin, can be readily manufactured by persons of ordinary skill in the art by adapting conventional methods known within this field in accordance with the description provided herein.

Another aspect of the invention is directed to a method for prophylaxis or treatment of a subject for a medical condition associated with or linked to an NADPH oxidase activity. The method comprises the step of administering one or more isolated phycobilins to a subject in a prophylactically or therapeutically effective amount for prophylaxis or treatment of a medical condition associated with or linked to an NADPH oxidase activity. The medical condition may be selected from the group consisting of ischemic heart disease, myocardial infarction, stroke, peripheral atherosclerosis, cerebrovascular atherosclerosis, left ventricular hypertrophy, congestive heart failure, arterial hypertension, pulmonary hypertension, erectile dysfunction, metabolic syndrome, diabetic retinopathy, diabetic neuropathy, diabetic nephropathy, glomerulosclerosis, pulmonary emphysema, asthma, allergy, osteoporosis, osteoarthritis, gastric ulcer, septic shock, fibrosis, pulmonary fibrosis, hepatic fibrosis, Parkinson's disease, Alzheimer's dementia, UV damage to the skin, cancer, rheumatoid arthritis, ulcerative colitis, scleroderma, pathological angiogenesis, transplant rejection, and chronic pain syndrome/hyperalgesia. In a preferred mode of this aspect of the invention, the phycobilin is selected from the group consisting of phycocyanobilin, phycoerythrobilin, phytochromobilin, each phycobilin optionally including a peptide fragment of a phycocyanin conjugated thereto. The phycobilin may be administered orally, parenterally, or topically.

BRIEF DESCRIPTION OF DRAWINGS

FIGS. 1A and 1B illustrate the inhibition by a phycobilin extract of NADPH oxidase in human aortic endothelial cells. Human cell cultures derived from aortic endothelium were incubated with NADPH to induce superoxide production by cellular NADPH oxidase. Superoxide production was quantified by lucigenin chemiluminescence. Lucigenin is a specific detector of superoxide. Diphenyleneiodonium (DPI), a known inhibitor of NADPH oxidase, was shown to completely inhibit the excess superoxide production induced by added NADPH. Phycocyanobilin (PCB, FIG. 1A) or biliverdin (BVD, FIG. 1B) were added to the NADPH-treated cell cultures in concentrations ranging from 300 nM to 20 µM. Biliverdin is another known inhibitor of NADPH oxidase. Phycocyanobilin and biliverdin both showed a dose-dependent inhibition of NADPH oxidase superoxide production. The inhibitory effect of 20 µM phycocyanobilin on NADPH oxidase activity in the human aortic endothelial cells was equivalent to that of DPI.

FIGS. 2A and 2B illustrate the inhibition by a phycobilin extract of NADPH oxidase in human aortic smooth muscle cells. Human cell cultures derived from aortic smooth muscle were incubated with NADPH to induce superoxide production by cellular NADPH oxidase. Superoxide production was quantified by lucigenin chemiluminescence. Lucigenin is a specific detector of superoxide. Diphenyleneiodonium (DPI), a known inhibitor of NADPH oxidase, was shown to completely inhibit the excess superoxide production induced by added NADPH. Phycocyanobilin (PCB, FIG. 2A) or biliverdin (BVD, FIG. 2B) were added to the NADPH-treated cell cultures in concentrations ranging from 300 nM to 20 µM. Biliverdin is another known inhibitor of NADPH oxidase. Phycocyanobilin and biliverdin both showed a dose-dependent inhibition of NADPH oxidase superoxide production. The inhibitory effect of 20 µM phycocyanobilin on NADPH oxidase activity in the human aortic smooth muscle cells was equivalent to that of DPI.

FIGS. 3A and 3B illustrate the inhibition by a phycobilin extract of NADPH oxidase activity in human renal mesangial cells. Human cell cultures derived from renal mesangial tissue were incubated with NADPH to induce superoxide production by cellular NADPH oxidase. Superoxide production was quantified by lucigenin chemiluminescence. Lucigenin is a specific detector of superoxide. Diphenyleneiodonium (DPI), a known inhibitor of NADPH oxidase, was shown to completely inhibit the excess superoxide production induced by added NADPH. Phycocyanobilin (PCB, FIG. 3A) or biliverdin (BVD, FIG. 3B) were added to the NADPH-treated cell cultures in concentrations ranging from 300 nM to 20 µM. Biliverdin also functions to inhibit of NADPH oxidase, as it is converted intracellularly to bilirubin. Phycocyanobilin and biliverdin both showed a dose-dependent inhibition of NADPH oxidase superoxide production. The inhibitory effect of 20 µM phycocyanobilin on NADPH oxidase activity in the human renal mesangial cells was less than that of DPI, but was statistically significant.

FIG. 4A depicts the homologous chemical structures of biliverdin and the chief phycobilins: phycocyanobilin, phytochromobilin, and phycoerythrobilin. FIG. 4B depicts the homologous chemical structures of bilirubin and the phycorubins: phycocyanorubin, phytochromorubin, and phycoerythrorubin. The arrows represent the catalytic activity of biliverdin reductase, present in mammalian cells.

DETAILED DESCRIPTION

Figure 4:
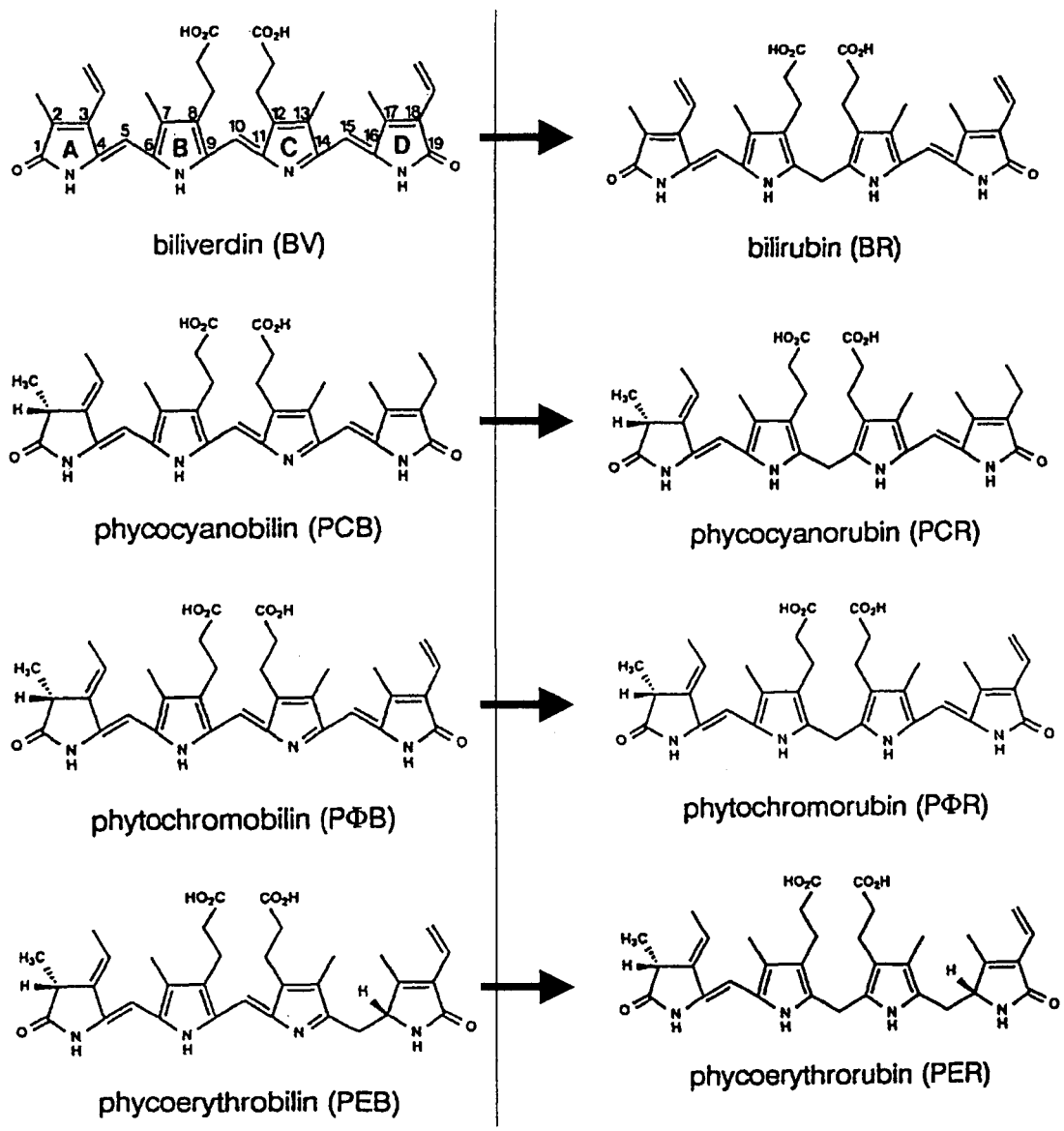
FIGS. 4A and 4B illustrate the conversion of biliverdin and phycobilins to bilirubin and phycorubins mediated by biliverdin reductase.

It is disclosed herein that phycorubins directly and potently inhibit the enzyme NADPH oxidase and that phycobilins, when administered to mammalian subjects or otherwise placed into contact with the enzyme biliverdin reductase, are converted to phycorubins. Accordingly, phycobilins serve as prodrugs or precursors of phycorubins and can be employed for the prophylaxis or treatment of medical conditions associated with or linked to an NADPH oxidase activity.

Phycobilins are a family of chromophore compounds found in plants, algae and cyanobacteria. The preferred phycobilins for use herein comprise phycocyanobilin, phycoerythrobilin, and phytochromobilin. In nature, phycobilins are covalently conjugated to apoproteins; the resulting holoproteins, referred to as phycocyanins, function to harvest light energy.

1. Definitions

NADPH oxidase refers to an enzyme complex that oxidizes the reduced form of nicotinamide adenine dinucleotide phosphate (NADP), concurrently reducing molecular oxygen to superoxide.

As defined herein, the term "isolated" denotes that the subject compound(s) have been substantially purified away from the milieu in which the subject compound(s) occur in nature. For example, in nature, phycobilins are conjugated to apoproteins wherein the apoprotein conjugated forms are referred to as phycocyanins, therefore, in one embodiment herein, isolated denotes that the thioether bonds linking phycobilins to phycocyanin apoproteins have been cleaved, and the resulting free phycobilins extracted and concentrated, such that the resulting concentrate is essentially free of phycocyanin holoprotein or apoprotein.

As defined herein, the term "phycochemical composition" denotes a composition that is derived from a plant or fruit.

As defined herein, the term "nutraceutical composition" denotes a processed food for which a medicinal effect on human health is claimed, or, alternatively, composition having a chemical component present in a conventional food.

As defined herein, the term "nutrient substance" denotes a chemical component present in a conventional food and having nutritional value.

As defined herein, the term "cosmeceutical composition" denotes a cosmetic for which a medicinal effect or drug-like benefit on human health is claimed.

As defined herein, the term "cosmetic substance" denotes any functional chemical component present in a conventional cosmetic that imparts a cosmetic property.

As defined herein, the term "topical administration" denotes any mode of delivery wherein a bio-active substance is applied to the skin.

As defined herein, the term "emollient carrier" denotes any carrier or ointment capable of carrying a substance and that is externally applied to the skin so as to soften or soothe the skin. Often, the "emollient carrier" soften or soothe the skin by preventing or slowing water loss. Most natural oils perform this function. For a review of conventional techniques for manufacturing emollient carriers employable with the present invention, see: Nair B. "Cosmetic Ingredients Review Expert Panel. Final report . . . " *International Journal of Toxicology.* 22 Suppl 2:11-35, 2003.

As defined herein, the term "sunscreen" denotes any substance that helps protect the skin from the sun's harmful rays by reflecting, absorbing, and/or scattering both ultraviolet A and B radiation.

As defined herein, the term "capsule" denotes any structure employed in the manufacture of pharmaceuticals for enclosing a bio-active substance in a relatively stable shell, allowing them to, for example, be taken orally or be used as a suppository. The two main types of capsules are hard-shelled capsules, which are normally used for dry, powdered ingredients, and soft-shelled capsules, primarily used for oils and for active ingredients that are dissolved or suspended in oil. Both of these classes of capsule have a gelatinous case, made either from gelatine or from plant-based gelling substances like carrageenans and/or modified forms of starch, cellulose, and functionally equivalent substances. For a review of conventionally encapsulation techniques employable for practicing the invention disclosed herein, see: Bill Bennett and Graham Cole (2003). *Pharmaceutical Production, an Engineering Guide.* IChemE, 126-129.

As defined herein, the term "tablet" denotes any mixture of active substances and excipients, in powder, pressed or compacted into a solid by conventional means. The excipients include binders, glidants (flow aids) and lubricants to ensure efficient tabletting; disintegrants to ensure that the tablet breaks up in the digestive tract; sweeteners or flavors to mask the taste of bad-tasting active ingredients; and pigments to make uncoated tablets visually attractive. A coating may be applied to hide the taste of the tablet's components, to make the tablet smoother and easier to swallow, and to make it more resistant to the environment, extending its shelf life.

As defined herein, the term "physiologically acceptable sterile solution suitable for injection" denotes any solution that is harmless when injected into a human subject and that is capable of carrying and delivering a bio-active substance of interest.

In one embodiment, the phycocyanins are digested, or partially digested (for example, with trypsin or other protease), forming free peptides and peptides conjugated to the phycobilins, wherein substantially purified peptide conjugated phycobilins are useful in the embodiments of the present invention. In the present embodiment, isolated means that the isolated phycobilin composition does not include phycobilins conjugated to the entire polypeptide of the apoprotein to which the phycobilins are found conjugated in nature (except in trace amounts, in one embodiment). In one embodiment regarding peptide phycobilin conjugates, the peptide is 100 amino acids in length or less. In one embodiment regarding peptide phycobilin conjugates, the peptide is 75 amino acids in length or less. In one embodiment regarding peptide phycobilin conjugates, the peptide is 50 amino acids in length or less. In one embodiment regarding peptide phycobilin conjugates, the peptide is 25 amino acids in length or less. In one embodiment regarding peptide phycobilin conjugates, the peptide is 10 amino acids in length or less.

Substantially purified denotes that the subject compound(s) comprise at least fifteen percent or more of the dry weight of a composition containing the subject compound(s). In one embodiment, substantially purified denotes that the subject compound(s) comprise at least twenty-five percent or more of the dry weigh of a composition containing the subject compound(s). In one embodiment, isolated denotes the subject compound(s) comprise fifty percent or more of the dry weight of a composition containing the subject compound(s). In one embodiment, isolated denotes the subject compound(s) comprise seventy-five percent or more of the dry weight of a composition containing the subject compound(s). In one embodiment, isolated denotes the subject compound(s) comprise ninety percent or more of the dry weight of a composition containing the subject compound(s). In one embodiment, isolated denotes the subject compound(s) comprise ninety-five percent or more of the dry weight of a composition containing the subject compound(s). In one embodiment, isolated denotes that the subject compound(s) are essentially pure.

In one embodiment, a therapeutically effective amount is an amount that inhibits NADPH oxidase activity by five percent or more. In one embodiment, a therapeutically effective amount is an amount that inhibits NADPH oxidase activity by ten percent or more. In one embodiment, a therapeutically effective amount is an amount that inhibits NADPH oxidase activity by fifteen percent or more. In one embodiment, a therapeutically effective amount is an amount that inhibits NADPH oxidase activity by twenty percent or more. In one embodiment, a therapeutically effective amount is an amount that inhibits NADPH oxidase activity by twenty-five percent or more. In one embodiment, a therapeutically effective amount is an amount that inhibits NADPH oxidase activity by thirty percent or more. In one embodiment, a therapeutically effective amount is an amount that inhibits NADPH oxidase activity by forty percent or more. In one embodiment, a therapeutically effective amount is an amount that inhibits NADPH oxidase activity by fifty percent or more.

In one embodiment, a therapeutically effective amount is 1 mg to 5000 mg of one or more phycobilins or one or more peptide-phycobilin conjugates administered per day. In one embodiment, a therapeutically effective amount is 1 mg to 2000 mg of one or more phycobilins or one or more peptide-phycobilin conjugate administered per day. In one embodiment, a therapeutically effective amount is 1 mg to 1000 mg of one or more phycobilins or one or more peptide-phycobilin conjugate administered per day. In one embodiment, a therapeutically effective amount is 100 mg to 5000 mg of one or more phycobilins or one or more peptide-phycobilin conjugate administered per day. In one embodiment, a therapeutically effective amount is 100 mg to 2000 mg of one or more phycobilins or one or more peptide-phycobilin conjugate administered per day.

In one embodiment, a prophylactic amount is an amount that inhibits NADPH oxidase activity by five percent or more. In one embodiment, a prophylactic amount is an amount that inhibits NADPH oxidase activity by ten percent or more. In one embodiment, a prophylactic amount is an amount that inhibits NADPH oxidase activity by fifteen percent or more. In one embodiment, a prophylactic amount is an amount that inhibits NADPH oxidase activity by twenty percent or more. In one embodiment, a prophylactic amount is an amount that inhibits NADPH oxidase activity by twenty-five percent or more. In one embodiment, a prophylactic amount is an amount that inhibits NADPH oxidase activity by thirty percent or more. In one embodiment, a prophylactic amount is an amount that inhibits NADPH oxidase activity by forty percent or more. In one embodiment, a prophylactic amount is an amount that inhibits NADPH oxidase activity by fifty percent or more.

In one embodiment, a prophylactic amount is 1 mg to 5000 mg of one or more phycobilins or one or more peptide-phycobilin conjugates administered per day. In one embodiment, a prophylactic amount is 1 mg to 2000 mg of one or more phycobilins or one or more peptide-phycobilin conjugate administered per day. In one embodiment, a prophylactic amount is 1 mg to 1000 mg of one or more phycobilins or one or more peptide-phycobilin conjugate administered per day. In one embodiment, a prophylactic amount is 100 mg to 5000 mg of one or more phycobilins or one or more peptide-phycobilin conjugate administered per day. In one embodiment, a prophylactic amount is 100 mg to 2000 mg of one or more phycobilins or one or more peptide-phycobilin conjugate administered per day.

A condition is any medical disease, disorder, syndrome, or the like.

2. Bilirubin is an Inhibitor of NADPH Oxidase Activity and is Useful in the Treatment and/or Prophylaxis of Conditions Linked to Oxidative Stress Produced from the NADPH Oxidase Activity.

A physiological inhibitor of NADPH oxidase is bilirubin (Lanone S et al., FASEB J 2005; 19:1890-2; Matsumoto H et al., Mol Cell Biochem 2006; April 20 epub; Jiang F et al., Hypertension 2006; 48:1-8) which is produced in the body by the reduction of biliverdin by the enzyme biliverdin reductase. Biliverdin, in turn, is produced by the activity of heme oxygenase which converts heme to biliverdin, carbon monoxide, and free ferrous iron.

The potent inhibitory activity of bilirubin on NADPH oxidase—observed in nanomolar intracellular concentrations—is reflected in numerous epidemiological studies correlating increased serum free bilirubin levels with reduced risk for atherosclerotic disease and cancer (Schwertner H A et al., Clin Chem 1994; 40:18-23; Novotny L et al., Exp Biol Med 2003; 228:568-71; Temme E H et al., Cancer Causes Control 2001; 12:887-94; Zucker S D et al., Hepatology 2004; 40:827-35; Ching S et al., J Nutr 2002; 132:303-6). For example, in the human genetic variant known as Gilbert syndrome, reduced expression of hepatic UDP-glucuronosyltransferase type 1A1 (the primary mediator of bilirubin conjugation) leads to a several-fold increase in serum free bilirubin which is associated with a markedly lower risk for coronary disease (Vitek L, et al., Atherosclerosis 2002; 160:449-56; Vitek L, et al., Cerebrovascular Dis 2006; 21:408-14). Furthermore, high-expression polymorphisms of the heme oxygenase-1 gene (HO-1, an inducible form of heme oxygenase) are linked to decreased risk for disorders in which oxidants play a key pathogenic role, reflecting the protection afforded by increased tissue levels of bilirubin in conditions including vascular disease, cancer, and inflammation-linked pathologies (Shibahara S, Tohoku J Exp Med 2003; 200:167-86; Exner M et al., Free Radical Biol Med 2004; 37:1097-1104; Kikuchi A et al., Hum Genet 2005; 116:354-60) Strikingly, high-expression polymorphisms of HO-1 have been linked to increased overall longevity in the Japanese population (Yamaya M et al., J Med Genet 2003; 40:146-80). These observations suggest that partial inhibition of NADPH oxidase activity are useful in the treatment and/or prophylaxis of conditions linked to oxidative stress resulting from NADPH oxidase activity.

Biliverdin is far more soluble than bilirubin, and within the body is efficiently converted to bilirubin by the ubiquitously expressed enzyme biliverdin reductase (Baranano D E et al., Proc Natl Acad Sci 2002; 99:16093; Sedlak T W et al., Pediatrics 2004; 113:1776-82). Because of its solubility, biliverdin has greater bioavailability than bilirubin upon oral administration, and indeed oral biliverdin has shown intriguing physiological effects in rodent studies that likely are mediated by inhibition of NADPH oxidase (Nakao A et al., Circulation 2005; 112:587-91; Sarady-Andrews J K et al., Am J Physiol Lung Cell Mol Physiol 2005; 289:L1131-7; Rodella L et al., Free Radic Biol Med 2006; 40:2198-205; Yamashita K et al., FASEB J 2004; 18:765-7; Nakao A et al., Gastroenterology 2004; 127:595-606; Fondevila C et al., Hepatology 2004; 40:1333-41; Nakao A et al., Am J Transplant 2005; 5:282-91; Berberat P O et al., Inflamm Bowel Dis 2005; 11:350-9; Olinger R et al., Circulation 2005; 112:1030-9).

The daily endogenous production of bilirubin is on the order of 300-400 mg (Meyer U A, Schweiz Med Wochenschr 1975; 105:1165-8). Administration of exogenous bilirubin and/or biliverdin could be used to further inhibit NADPH oxidase activity over and above the inhibition observed by endogenous bilirubin and/or biliverdin and, thereby, could be used to treat or prevent conditions associated with NADPH oxidase activity. However, there is a limited commercial supply of bilirubin and biliverdin, as bilirubin is currently derived from ox bile, and biliverdin is produced by complex and costly organic synthesis. In other words, biliverdin is produced either by de novo synthesis, or by oxidizing pre-existing bilirubin. The latter strategy does little to make biliverdin commercially feasible, since it is dependent on scarce bilirubin.

The present inventors have noted that phycobilins are close structural analogs of biliverdin, reflecting the fact that phycobilins are derived biosynthetically from biliverdin or by oxidation of bilirubin (see FIG. 4). Further, the inventors found evidence that phycobilins are good substrates for biliverdin reductase, which converts them to compounds known as phycorubins that are close analogs of bilirubin (Terry M J et al., J Biol Chem 1993; 268:26099-106).

The inventors discovered, in part, that phycorubins administered as their phycobilin precursors to mammalian cells (which contain biliverdin reductase) inhibits cellular NADPH oxidase activity. This discovery is demonstrated by the data presented from cell culture studies in FIGS. 1, 2, and 3.

Therefore, phycobilins are useful in one embodiment of the present invention for inhibiting the production of reactive oxygen species in mammalian cells and tissues and are useful in certain embodiments for preventing and/or treating any condition associated with NADPH oxidase activity.

Furthermore, inasmuch as phycobilins constitute up to 1% of the dry weight of certain cyanobacteria such as Spirulina (Patel A et al., Protein Express Purification 2005; 40:248-55), their production in bulk is practical.

Like bilirubin, biliverdin, and hundreds of other phycochemicals, phycobilins have been reported to act as versatile oxidant scavengers in cell-free systems (Hirata T et al., J Appl Phycology 2000; 12:435-9). However, there are no previous reports or suggestions that phycobilins can inhibit NADPH oxidase. Indeed, to the best of the inventors' knowledge, there have been no previous studies in which isolated phycobilins have been administered to humans, animals, or mammalian cell cultures. Also, there have been no previous suggestions that isolated phycobilins could be used in dietary supplements, functional foods, or cosmetics.

Plants do not have biliverdin reductase. Mammalian cells and tissues universally express biliverdin reductase.

3. Phycobilin Compositions

Phycobilin compositions may be manufactured in any manner that is known in the art (including, e.g., by conventional mixing, dissolving, granulating, dragee making, emulsifying, encapsulating, entrapping, lyophilizing, or suspending processes). It is preferred that manufacture is according to Good Manufacturing Practice, the procedures and regulations of which are known in the art. In one embodiment the phycobilin is food grade. In one embodiment the phycobilin is human food grade.

In certain embodiments, the phycobilin composition is manufactured to further include a pharmaceutically acceptable carrier, excipient, auxiliary, preservative, or other ingredient (referred to collectively herein as a "pharmaceutically acceptable carrier"). The term "carrier" refers herein to a "pharmaceutically acceptable carrier" and includes food grade fillers. Preferably, a pharmaceutically acceptable carrier is suitable for administration to a human or a non-human mammal. Further details on techniques for formulation and administration of pharmaceutical compositions may be found in the latest edition of Remington's Pharmaceutical Sciences (Maack Publishing Co., Easton, Pa.).

Fluid carriers may include aqueous solutions, preferably in physiologically compatible buffers (e.g., Hanks' solution, Ringer's solution, or physiologically buffered saline). Fluid carriers also include non-aqueous and oily suspensions. Suitable lipophilic solvents or vehicles may include fatty oils (e.g., sesame oil, synthetic fatty acid esters, ethyl oleate, triglycerides, or liposomes). Useful liposomes include cationic liposomes, anionic liposomes, and liposomes with neutral charge density. Viscosity enhancing agents may be included (e.g., sodium carboxymethyl cellulose, sorbitol, or dextran). Stabilizers, adhesives, or agents which increase solubility may also be included. Additional inert ingredients may include any or all of gum arabic, syrup, lanolin, or starch. Another excipient which may be used is polyethylene glycol (PEG). PEG can be admixed with the formulation or linked to the phycobilin molecule itself. PEG may be useful, for example, as a dehydrating or concentrating agent. Accordingly, carriers may be aqueous, non-aqueous (hydrophobic), or amphiphilic. Delayed release and/or sustained release carriers, and the pharmaceutical formulations thereof, are known in the art and can be used in embodiments herein, in light of the present disclosure.

The phycobilin composition may be provided as a salt and can be formed with an acid (e.g., hydrochloric, sulfuric, acetic, lactic, tartaric, malic, succinic, and the like). In another embodiment, the phycobilin composition may be a lyophilized powder which is preferably combined with buffer prior to use.

The phycobilin may be incorporated into a lotion base, face mask base, shampoo base, conditioner base, skin toner base, or other cosmetic base to form a cosmetic comprising a phycobilin (or isolated phycobilin). The cosmetic containing the phycobilin is useful, for example, for reducing oxidative damage of the hair, skin, and the like.

4. Administering a Phycobilin Composition

The phycobilin compositions may be administered by any desirable route including, but not limited to, oral, intravenous, intramuscular, nasal, intratracheal, intra-articular, intra-arterial, intramedullary, intrathecal, intraventricular, transdermal, subcutaneous, intraperitoneal, intranasal, intratumoral, enteral, topical, sublingual, vaginal, or rectal routes of administration. In light of the present invention, one of ordinary skill in the art is able to select a suitable route for administering a phycobilin composition to a subject.

5. Dosage of a Phycobilin Composition

In light of the present invention and knowledge in the art, the determination of an effective dose of a phycobilin composition is well within the capability of those skilled in the art.

A therapeutically effective dose or range can be estimated initially either in cell culture assays or in animal models; usually in mice, rats, rabbits, dogs, pigs, or non-human primates. The animal model may also be used to determine the preferred concentration range and route of administration. Such information can then be used to select preferred doses and routes for administration in humans.

Therapeutic efficacy and toxicity may be determined by standard pharmaceutical procedures in cell cultures, experimental animals, or other transplant model systems. For example, the ED50 (the dose therapeutically effective in 50% of the population) and the LD50 (the dose lethal to 50% of the population) can be determined in a model system. The dose ratio between toxic and therapeutic effects is the therapeutic index, which may be expressed as the ratio, LD50/ED50. Phycobilin compositions which exhibit large therapeutic indices are preferred. The data obtained from the model system(s) is used in formulating a range of dosage for human use. The dosage contained in such compositions is preferably within a range of circulating concentrations that include the ED50 with low toxicity or, more preferably, essentially no toxicity. Accordingly, the dosage of the phycobilin composition that is used in a subject is preferably determined by the practitioner, in light of factors related to the subject that requires treatment.

Dosage and administration are adjusted to provide sufficient levels of the active moiety(ies) (e.g., circulating and/or local concentration) or to maintain the desired effect. Factors which may be taken into account include the severity of the disease state, general health of the subject, age, weight, gender, diet, time and frequency of administration, drug combination(s), reaction sensitivities, tolerance to therapy, and response to therapy.

The following Examples are meant to further explain embodiments of the invention without limiting the invention. Dosage Considerations: Comparisons with Spirulina and Phycocyanobilin:

Phycocyanin constitutes about 14% of the total dry weight of spirulina; phycocyanobilin (PCB) represents about 4.7% of the mass of phycocyanin (Padyana A K, et al. Crystal structure of a light-harvesting protein C-phycocyanin from Spirulina platensis. *Biochem Biophys Res Commun* 2001 Apr. 13; 282(4):893-8.). It follows that about 0.66% of the dry mass of spirulina is PCB. In other words, 15 g of spirulina—approximately a heaping tablespoon—contains about 100 mg PCB.

Assuming that absorption and metabolism of spirulina-bound PCB is similar in rodents and humans, then clinically useful dose regimens of spirulina (and perhaps PCB) can be estimated by extrapolating from regimens that demonstrate antioxidant efficacy in rodents. Such dose extrapolation can be done straightforwardly on a mg/kg basis. However, in clinical practice, dose is often adjusted by relative body surface area, which corresponds to the ⅔ power of the ratio of body weights. This latter standard evidently yields a much lower correction factor. A commonly employed compromise between these two standards is to adjust dose by the ¾ power of the ratio of body weights; this has been found to offer a "best fit" when extrapolating various quantifiable metabolic paramters between mammalian species. (Travis C C. Interspecies extrapolation in risk analysis. *Ann 1st Super Sanita* 1991; 27(4):581-93; Darveau C A, et al., Allometric cascade as a unifying principle of body mass effects on metabolism. *Nature* 2002 May 9; 417(6885):166-70; Lindstedt L, et al. Use of allometry in predicting anatomical and physiological parameters of mammals. *Lab Anim* 2002 January; 36(1):1-19) The ¾ power standard yields a correction factor of about 80 if comparing a 200 g rat with a 70 kg human; or a factor of 450 if comparing a 20 g mouse with a 70 kg human. (In other words, if a rat receives×mg of an agent, the corresponding human dose would be 80× mg.) In an extensive series of investigations, Romay and colleagues have reported that oral phycocyanin administered orally to mice and rats exerts a number of dose-dependent anti-inflammatory effects in a dose range of 50-300 mg/kg/day. (Romay C, et al., Antioxidant and anti-inflammatory properties of C-phycocyanin from blue-green algae. *Inflamm Res* 1998 January; 47(1):36-41; Romay C, et al., Effects of phycocyanin extract on tumor necrosis factor-alpha and nitrite levels in serum of mice treated with endotoxin. *Arzneimittelforschung* 2001 September; 51(9):733-6; Romay C, et al., C-phycocyanin: a biliprotein with antioxidant, anti-inflammatory and neuroprotective effects. *Curr Protein Pept Sci* 2003 June; 4(3):207-16; Rimbau V, et al., Protective effects of C-phycocyanin against kainic acid-induced neuronal damage in rat hippocampus. *Neurosci Lett* 1999 Dec. 3; 276(2):75-8.) This amounts to a PCB intake of 2.35-14.1 mg/kg. If extrapolated on a mg/kg basis, this corresponds to a daily intake of 165-990 mg in a 70 kg human. Extrapolation by the ¾ power standard gives human daily intakes of 21.2-127 mg (using mice) and 37.6-226 mg (using rats).

Recent studies in which whole spirulina has been administered orally to rodents have also shown anti-inflammatory effects, in doses ranging from 150-1,000 mg/kg/day. (Remirez D, et al., Inhibitory effects of Spirulina in zymosan-induced arthritis in mice. *Mediators Inflamm* 2002 April; 11(2):75-9; Rasool M, et al., Anti-inflammatory effect of Spirulina fusiformis on adjuvant-induced arthritis in mice. *Biol Pharm Bull* 2006 December; 29(12):2483-7; Chamorro G, et al., Spirulina maxima pretreatment partially protects against 1-methyl-4-phenyl-1,2,3,6-tetrahydropyridine neurotoxicity. *Nutr Neurosci* 2006 October; 9(5-6):207-12; Khan M, et al., Protective effect of Spirulina against doxorubicin-induced cardiotoxicity. *Phytother Res* 2005 December; 19(12):1030-7; Mohan I K, et al., Protection against cisplatin-induced nephrotoxicity by Spirulina in rats. *Cancer Chemother Pharmacol* 2006 December; 58(6):802-8; Khan M, et al., Spirulina attenuates cyclosporine-induced nephrotoxicity in rats. *J Appl Toxicol* 2006 September; 26(5):444-51) This amounts to intakes of 1-6.6 mg/kg/day PCB. Extrapolating on the basis of relative weight, this corresponds to an intake of 70-462 mg PCB in a 70 kg human. Extrapolating on the basis of the ¾ power standard, it corresponds to an intake of 9-59 mg (mouse stuidies) or 16-106 mg (rat studies). The syndromes in which spirulina demonstrated protective efficacy included adjuvant arthritis, MPTP-induced Parkinsonism, doxorubicin-induced cardiomyopathy, and nephropathy mediated by cisplatin and cyclosporine; it is unlikely to be coincidental that activation of NADPH oxidase has been shown to be a key mediator of each of these syndromes. (Bart B A, et al., The newly developed neutrophil oxidative burst antagonist apocynin inhibits joint-swelling in rat collagen arthritis. *Agents Actions Suppl* 1991; 32:179-84; van Lent P L, et al., NADPH-oxidase-driven oxygen radical production determines chondrocyte death and partly regulates metalloproteinase-mediated cartilage matrix degradation during interferon-gamma-stimulated immune complex arthritis. *Arthritis Res Ther* 2005; 7(4):R885-R895; Miesel R, et al., Antiinflammatory effects of NADPH oxidase inhibitors. *Inflammation* 1995 June; 19(3):347-62; Hougee et al., Oral administration of the NADPH-oxidase inhibitor apocynin partially restores diminished cartilage proteoglycan synthesis and reduces inflammation in mice. *Eur J Pharmacol* 2006 February 15; 531(1-3):264-9.)

As noted, a heaping tablespoon of spirulina contains approximately 100 mg PCB. Thus, a regimen of two heaping tablespoons per day—arguably the highest intake that would be feasible on a long-term basis with well-motivated patients—would provide about 200 mg PCB daily. This intake is thus within—and in some instances a bit beyond— the extrapolated dose ranges noted above. It should follow that—assuming that humans digest and metabolize spirulina-bound PCB much like rodents do—a daily intake of 2 heaping tablespoons of spirulina daily should have clinically useful antioxidant activity in humans. Whereas it might prove clinically feasible to use whole spirulina as a strategy for inhibiting NADPH oxidase, this entails practical difficulties owing to the bulk and foul odor and taste of the high spirulina doses required. Thus, there is a need for supplements providing isolated phycobilins.

EXAMPLES

1. Preparation of Phycobilin Compositions

Phycocyanobilin was prepared from 20 grams of dry spirulina algae, using hot methanol extraction as described previously (O Carra P et al, Phytochemistry 1966; 5:993-7). The algae was extracted three times with methanol at room temperature to remove chlorophyll and carotenoids. After filtration, the solid, which still retained the protein-bound phycocyanobilin, was transferred into 250 ml flask, suspended in methanol (160 ml) containing ascorbic acid (1.6 g), and stirred at 60° C. Under these conditions, methanolysis gradually cleaves the thioether bonds linking phycocyanobilin to the phycocyanin apoprotein. After 8 hr the filtered extract was evaporated under reduced pressure at 40° C. The residue was dissolved in a small volume of methanol and added into ethyl acetate/hexane (1/1); the organic phase was extracted three times with 0.1N HCl. The combined acid extracts were washed with ethyl acetate/hexane (1/1), and neutralized with solid sodium acetate; the blue pigment was extracted three times into ethyl acetate/hexane, and the combined extracts were washed with 1% sodium acetate. The blue pigment was then re-extracted from the organic phase into 0.1N HCl and finally extracted into chloroform (50 ml×2). The chloroform extracts were dried over anhydrous sodium sulfate and evaporated under reduced pressure at 40° C. The oily residue was dissolved in a small volume of ethyl acetate, transferred into a vial (4 ml), and treated with an excess of hexane. The precipitated pigment was centrifuged and the pellet was re-dissolved in a small volume of ethyl acetate and precipitated again with an excess of hexane. After centrifugation the pellet was dried under high vacuum. 12 mg of essentially pure phycocyanobilin were obtained.

The obtained phycocyanobilin sample was analyzed using a Waters 600E HPLC system: C8 column (Varian), acetonitrile/ammonium phosphate (0.1M, pH 2.5) as a mobile phase, and detection was at 375 nm. The analysis showed one main product of phycocyanobilin.

2. Phycobilin Extract Inhibits NADPH Oxidase in Human Aortic Endothelial Cells Human cell cultures derived from aortic endothelium were incubated with NADPH to induce superoxide production by cellular NADPH oxidase. Superoxide production was quantified by lucigenin chemiluminescence. Lucigenin is a specific detector of superoxide. Diphenyleneiodonium (DPI), a known inhibitor of NADPH oxidase, was shown to completely inhibit the excess superoxide production induced by added NADPH. Phycocyanobilin (PCB, FIG. 1A) or biliverdin (BVD, FIG. 1B) were added to the NADPH-treated cell cultures in concentrations ranging from 300 nM to 20 µM. Biliverdin is another known inhibitor of NADPH oxidase. Phycocyanobilin and biliverdin both showed a dose-dependent inhibition of NADPH oxidase superoxide production. The inhibitory effect of 20 µM phycocyanobilin on NADPH oxidase activity in the human aortic endothelial cells was equivalent to that of DPI.

Experimental

Human aortic endothelial cells were purchased from Clonetics (East Rutherford, N.J.). The endothelial cell were cultured in endothelial cell basal medium (Clonetics) supplemented with hFGF-B, VEGF, IGF-1, ascorbic acid hEGF, hydrocortisone and 2% fetal calf serum. The cells from 2nd to 5th passages were used in the experiments. Cellular production of superoxide anion was determined by the lucigenin method. For the experiments, cells were detached with trypsin/EDTA and resuspended in modified HEPES buffer containing 140 mM NaCl, 5 mM KCl, 0.8 mM $MgCl_2$, 1.8 mM $CaCl_2$, 1 mM $Na_2HPO_4$, 25 mM HEPES, and 1% glucose (pH7.2), and incubated with or without various concentrations of phycocyanobilin (PCB) or biliverdin (BVD) from 300 nM to 20 µM for 1 h. Immediately before recording, NADPH (100 µM) and dark-adapted lucigenin (5 µM) were added to cell suspension. Light emission was recorded every minute for 20 min and was expressed as mean arbitrary light unit/min. Experiments were performed in triplicate. In experiments with inhibition of NAD(P)H oxidase, diphenylene iodonuim cloride (DPI, $10^{-5}$ M), an inhibitor of NAD(P)H oxidase, was added 10 min before NADPH addition and recording of chemiluminescence. This is the first experiment to see the effect of purified phycocyanobilin on NADPH oxidase activity using human aortic endothelial cells.

3. Phycobilin Extract Inhibits NADPH Oxidase in Human Aortic Smooth Muscle Cells Human cell cultures derived from aortic smooth muscle were incubated with NADPH to induce superoxide production by cellular NADPH oxidase. Superoxide production was quantified by lucigenin chemiluminescence. Lucigenin is a specific detector of superoxide. Diphenyleneiodonium (DPI), a known inhibitor of NADPH oxidase, was shown to completely inhibit the excess superoxide production induced by added NADPH. Phycocyanobilin (PCB, FIG. 2A) or biliverdin (BVD, FIG. 2B) were added to the NADPH-treated cell cultures in concentrations ranging from 300 nM to 20 µM. Biliverdin is another known inhibitor of NADPH oxidase. Phycocyanobilin and biliverdin both showed a dose-dependent inhibition of NADPH oxidase superoxide production. The inhibitory effect of 20 µM phycocyanobilin on NADPH oxidase activity in the human aortic smooth muscle cells was equivalent to that of DPI.

Experimental

Human aortic smooth muscle cells were purchased from Clonetics (East Rutherford, N.J.). The smooth muscle cells were cultured in a Smooth Muscle Cell Growth Medium (Clonetics) containing 5% fetal calf serum. The cells from 2nd to 5th passages were used in the experiments. Cellular production of superoxide anion was determined by the lucigenin method. For the experiments, cells were detached with trypsin/EDTA and resuspended in modified HEPES buffer containing 140 mM NaCl, 5 mM KCl, 0.8 mM $MgCl_2$, 1.8 mM $CaCl_2$, 1 mM $Na_2HPO_4$, 25 mM HEPES, and 1% glucose (pH7.2), and incubated with or without various concentrations of phycocyanobilin (PCB) or biliverdin (BVD) from 300 nM to 20 μM for 1 h. Immediately before recording, NADPH (100 μM) and dark-adapted lucigenin (5 μM) were added to cell suspension. Light emission was recorded every minute for 20 min and was expressed as mean arbitrary light unit/min. Experiments were performed in triplicate. In experiments with inhibition of NAD(P)H oxidase, diphenylene iodonuim cloride (DPI, $10^{-5}$ M), an inhibitor of NAD(P)H oxidase, was added 10 min before NADPH addition and recording of chemiluminescence. This is the first experiment to see the effect of purified phycocyanobilin on NADPH oxidase activity using human aortic smooth muscle cells.

4. Phycobilin Extract Inhibits NADPH Oxidase in Human Renal Mesangial Cells

Human cell cultures derived from renal mesangial tissue were incubated with NADPH to induce superoxide production by cellular NADPH oxidase. Superoxide production was quantified by lucigenin chemiluminescence. Lucigenin is a specific detector of superoxide. Diphenyleneiodonium (DPI), a known inhibitor of NADPH oxidase, was shown to completely inhibit the excess superoxide production induced by added NADPH. Phycocyanobilin (PCB, FIG. 3A) or biliverdin (BVD, FIG. 3B) were added to the NADPH-treated cell cultures in concentrations ranging from 300 nM to 20 μM. Biliverdin is another known inhibitor of NADPH oxidase. Phycocyanobilin and biliverdin both showed a dose-dependent inhibition of NADPH oxidase superoxide production. The inhibitory effect of 20 μM phycocyanobilin on NADPH oxidase activity in the human renal mesangial cells was less than that of DPI, but was statistically significant.

Experimental

Human mesangial cells were purchased from Clonetics (East Rutherford, N.J.). The smooth muscle cells were cultured in a Mesangial Cell Growth Medium (Clonetics) containing 5% fetal calf serum. The cells from 2nd to 5th passages were used in the experiments. Cellular production of superoxide anion was determined by the lucigenin method. For the experiments, cells were detached with trypsin/EDTA and resuspended in modified HEPES buffer containing 140 mM NaCl, 5 mM KCl, 0.8 mM $MgCl_2$, 1.8 mM $CaCl_2$, 1 mM $Na_2HPO_4$, 25 mM HEPES, and 1% glucose (pH7.2), and incubated with or without various concentrations of phycocyanobilin (PCB) or biliverdin (BVD) from 300 nM to 20 μM for 1 h. Immediately before recording, NADPH (100 μM) and dark-adapted lucigenin (5 μM) were added to cell suspension. Light emission was recorded every minute for 20 min and was expressed as mean arbitrary light unit/min. Experiments were performed in triplicate. In experiments with inhibition of NAD(P)H oxidase, diphenylene iodonuim cloride (DPI, $10^{-5}$ M), an inhibitor of NAD(P)H oxidase, was added 10 min before NADPH addition and recording of chemiluminescence. This is the first experiment to see the effect of purified phycocyanobilin on NADPH oxidase activity using human renal mesangial cells.

Medical Conditions Associated with or Linked to an NADPH Oxidase Activity:

Ischemic heart disease is associated with or linked to an NADPH oxidase activity. Activation of NADPH oxidase in endothelial cells, vascular smooth muscle cells, and intimal macrophages plays a central role in the induction of the coronary atherosclerosis which underlies this syndrome. Numerous risk factors for ischemic heart disease—including elevated plasma levels of LDL cholesterol, C-reactive protein, and homocysteine, as well as arterial hypertension, are known to activate NADPH oxidase in vascular endothelial cells. The resulting increase in oxidant stress encourages intimal inflammation, in part by boosting NF-kappaB activation in endothelial cells, and also by antagonizing the protective anti-inflammatory, anti-hypertrophic, and anti-thrombotic activity of nitric oxide. Vascular oxidant stress also promotes LDL oxidation. Consistent with the potential anti-atherosclerotic activity of phycobilins, the feeding of phycocyanin to cholesterol-fed hamsters has been reported to inhibit the production of arterial fatty streaks quite markedly. Moreover, coronary disease appears to be relatively rare in people with Gilbert syndrome (a genetic variant characterized by elevated plasma levels of free bilirubin). There is widespread agreement among scientists expert in coronary disease that pharmacological inhibition of NADPH oxidase has considerable potential for prevention and treatment of this syndrome. (Soccio M et al., Eur J Clin Invest 2005; 35:305-14; Cai H et al., Trends Pharmacol Sci 2003; 24:471-8; Rueckschloss U et al., Antiox Redox Signal 2003; 5:171-80; Griendling K K et al., Circ Res 2000; 86:494-501; Meyer J W et al., FEBS Lett 2000; 472:1-4; Riss J, et al., J Agric Food Chem 2007; 55:7962-7; Vitek L, et al., Atherosclerosis 2002; 160:449-56; Vitek L, et al., Cerebrovasc Dis 2006; 21:408-14)

Myocardial Infarction is associated with or linked to an NADPH oxidase activity. Although activation of NADPH evidently contributes to risk for myocardial infarction by promoting the coronary atherosclerosis that is a precondition for this syndrome, it can also contribute to infarction more acutely by promoting plaque instability (reflecting, in part, activation of macrophage-derived proteolytic enzymes by oxidants) and platelet aggregation. Activation of NADPH oxidase in platelets contributes to the process of aggregation, and NADPH oxidase-derived superoxide from endothelium also promotes platelet aggregation less directly by antagonizing the platelet-stabilizing activity of nitric oxide. Moreover, activation of NADPH oxidase both in endothelium and in infiltrating inflammatory cells is known to be a mediator of the ischemia-reperfusion damage that promotes the death of myocardial cells in the infarcted zone. (Channon K M, Arterioscler Thromb Vasc Biol 2002; 22:1751-2; Rupin A et al., Cardiovascular Res 2004; 63:323-30; Chlopicki S et al., Antiox Redox Signal 2004; 6:691-8; Herkert O et al., Antiox Redox Signal 2004; 6:765-76)

Stroke is associated with or linked to an NADPH oxidase activity. While the activation of NADPH oxidase in cerebrovascular arteries contributes importantly to the structural remodeling of these arteries that contributes to the genesis of ischemic and possibly hemorrhagic stroke, NADPH oxidase activation within infarcted brain tissue as well as infiltrating leukocytes also potentiates the loss of brain neurons and functional incapacity that results. Thus, in rodents that are genetically deficient in NADPH oxidase activity, or that are pre-treated with an NADPH oxidase-inhibitory drugs such as apocynin or statins, the damage to brain tissue observed after temporary induction of ischemia is notably less severe. It is also likely that NADPH oxidase activation in platelets contributes to the formation of thrombi that trigger ischemic stroke. (Walder C E et al., Stroke 1997; 28:2252-8; Wang Q et al., Brain Res 2006; 1090:182-9; Miller A A et al., Brain Res 2006; 1111:111-6; Hong H et al., Am J Physiol Heart Circ Physiol 2006 Jun. 9 epub)

Peripheral and Cerebral Atherosclerosis is associated with or linked to an NADPH oxidase activity. While NADPH oxidase activation is clearly an important mediator of coronary atherogenesis, it also is a key mediator of atherogenesis in peripheral arteries—as commonly encountered in diabetics and smokers—and in cerebral arteries. (Meyer J W et al., FEBS Lett 2000; 472:1-4)

Left Ventricular Hypertrophy is associated with or linked to an NADPH oxidase activity. During the process of left ventricular hypertrophy (LVH), NADPH oxidase becomes activated in cardiomyocytes as well as vascular endothelial cells. There is cogent evidence that the resulting oxidant stress plays a crucial role in the activation of intracellular signaling pathways that promote cardiomyocyte hypertrophy, interstitial fibrosis, and the resultant chamber remodeling. (Li J M et al., Hypertension 2002; 40:477-84; Byrne J A et al., Circ Res 2003; 93:802-5; Murdoch C E et al., Cardiovasc Res 2006; 71:208-15)

Congestive Heart Failure is associated with or linked to an NADPH oxidase activity. Oxidant stress, derived in large measure from NADPH oxidase, is also a mediator of the cardiac dysfunction—reduced efficiency of both contraction and relaxation—that characterizes the decompensatory phase of heart failure in patients with LVH. (Murdoch C E et al., Curr Opin Pharmacol 2006; 6:148-53; MacCarthy P A, Circulation 2001; 104:2967-74; Takayama T et al., Circ J 2004; 68:1067-75; Heymes C et al., J Am Coll Cardiol 2003; 41:2164-710)

Arterial Hypertension is associated with or linked to an NADPH oxidase activity. Increased activation of NAPDH oxidase in endothelial cells and vascular smooth muscle cells is commonly observed in arterial hypertension, and contributes to the elevation of blood pressure by antagonizing the vasodilatory action of nitric oxide. This oxidative stress also is a mediator of angiotensin II signaling, and promotes the medial hypertrophy that frequently complicates longstanding hypertension. In the brain, activation of NADPH oxidase in centers that regulate sympathetic activity promotes elevation of sympathetic activity, a key mediator of the hypertension associated with obesity. Hypertension appears to be remarkably rare in subjects with Gilbert syndrome (Touyz R M et al, Histochem Cell Biol 2004; 122:339-52; Touyz R M et al, Clin Exp Pharmacol Physiol 2003; 24:471-8; Morawietz H et al., Biochem Biophys Res Comm 2001; 285:1130-5; Jung O et al., Circulation 2004; 109:1795-801; Zalba G et al., Hypertension 2001; 38:1395-9; Wang H D et al., Circ Res 2001; 88:947-53; Vitek L, et al., Atherosclerosis 2002; 160:449-56)

Pulmonary Hypertension is associated with or linked to an NADPH oxidase activity. The activity and expression of NADPH oxidase in intrapulmonary arteries is increased when chronic hypoxia induces pulmonary hypertension. This oxidant stress contributes both to the elevation in pulmonary blood pressure and the associated hypertrophic remodeling of pulmonary arteries and the right ventricle; thus, these phenomena are substantially diminished when mice genetically deficient in NADPH oxidase are exposed to chronic hypoxia. Treatment with agents that dismute superoxide are also protective in this regard. (Liu J Q et al, Am J Physiol Lung Cell Mol Physiol 2006; 290:L2-10; Brennan L A, et al., Circ Res 2003; 92:683-91)

Erectile Dysfunction is associated with or linked to an NADPH oxidase activity. Erectile dysfunction (ED) of vascular origin—the most common form—reflects a relative failure of nitric oxide-mediated vasodilation. Drugs used to treat ED typically compensate for this defect by suppressing the catabolism of cGMP (a key mediator of nitric oxide's vasodilatory activity.) There is now evidence that ED of vascular origin is associated with increased oxidant stress in the penile vasculature, and NADPH oxidase is likely to be the primary source of this stress. Morever, this oxidant stress may be largely responsible for the relative failure of nitric oxide bioactivity in vascular ED. This model rationalizes the great increase in risk for ED associated with vascular risk factors such as hyperlipidemia, hypertension, and diabetes. (Kouparis A et al, BJU Int 2004; 94:257-8; Jeremy J Y et al. J Urol 2006; 175-1175-6; Jeremy J Y et al., Int J Impot Res 2006; October 19 epub)

Metabolic Syndrome is associated with or linked to an NADPH oxidase activity. Overactivation of NADPH oxidase plays a key role in both the genesis and the pathological complications of metabolic syndrome. There is recent evidence that the insulin resistance which develops in hypertrophied adipocytes—and which induces systemic insulin resistance by promoting free fatty acid overexposure and dysregulation of adipocytokines—is dependent on an increase in adipocyte oxidative stress mediated by activated NADPH oxidase. Thus, apocynin treatment ameliorates insulin resistance syndrome in overweight fat-fed mice. Moreover, the free fatty acid overexposure that is characteristic of insulin resistance syndrome activates NAPDH oxidase in vascular endothelium, thereby promoting the marked increase in vascular risk associated with insulin resistance syndrome. Overactivation of NADPH oxidase in pancreatic beta cells in insulin-resistant subjects may contribute to the onset of beta cell dysfunction that can lead to type 2 diabetes. (Talior I et al., Am J Physiol Endocrinol Metab 2005; 288:E405-11; Furukawa S et al., J Clin Invest 2004; 114:1752-61; Inoguchi T et al., Curr Drug Targets 2005; 6:495-501; Delbosc S et al., Atherosclerosis 2005; 179:43-9; Roberts C K et al., Metabolism 2006; 55:928-34)

Diabetic Complications—Retinopathy, Neuropathy, Nephropathy is associated with or linked to an NADPH oxidase activity. Concurrent elevations of glucose and free fatty acids, as characteristically seen in diabetes, promote chronic activation of NAPDH oxidase in glucose-permeable cells (including vascular endothelium, retinal pericytes, and renal mesangial cells) by boosting activity of various isoforms of protein kinase C. The resultant oxidant stress is a key mediator of some of the most important long-term complications of diabetes—including retinopathy, neuropathy, nephropathy, and atherogenic vascular disease. Thus, agents which suppress activation of NADPH oxidase, including apocynin, have been shown to prevent mesangial hyperplasia and ameliorate neural dysfunction in diabetic rodents. A recent epidemiological study reveals that risk for retinopathy, kidney dysfunction, and coronary disease is nearly 80% less in diabetics who have Gilbert syndrome (associated with chronically elevated free bilirubin levels) as compared to diabetics who do not have this syndrome. Since free bilirubin functions physiologically to inhibit NADPH oxidase, this constitutes cogent indirect evidence that NADPH oxidase activation is a prominent mediator of diabetic complications in humans. (Inoguchi T et al., Curr Drug Targets 2005; 6:495-501; Inoguchi T et al., J Am Soc Nephrol 2003; 14:S227-32; Manea A et al, Biol Cell 2005; 97:123-34; Ushio-Fukai M et al, Mol Cell Biochem 2004; 264:85-97; Cotter M A et al, Life Sci 2003; 73:1813-24; Coppey L J et al, Free Radical Res 2003; 37:33-

400; Li J M et al, J Am Soc Nephrol 2003; 14:S221-6; Xia L et al., Am J Physiol Renal Physiol 2005; 290:F345-56; Lee H B et al., J Am Soc Nephrol 2003; 14:S241-5; Inoguchi T, et al., JAMA 2007; 298:1398-400)

Glomerulosclerosis is associated with or linked to an NADPH oxidase activity. Activation of NADPH oxidase in mesangial cells plays a pathogenic role in the glomerulosclerosis associated with chronic hypertension or autoimmune disorders. This hypertrophic response is mediated largely by increased activity of transforming growth factor-beta; oxidative stress generated by NADPH oxidase plays a key role in TGF-beta signal transduction, and also acts to boost expression of this hormone. Moreover, the anti-hypertrophic activity of nitric oxide is antagonized by oxidant stress. (Modlinger P S et al., Semin Nephrol 2004; 24:354-65; Kondo S et al., J Am Soc Nephrol 2006; 17:783-94; Yang Z Z et al., Kidney Int 2003; 63:1012-20; McCarty M F, Med Hypoth 2006; 67:1277-96)

Emphysema is associated with or linked to an NADPH oxidase activity. NADPH oxidase-derived oxidants also plays a pathogenic role in emphysema associated with chronic smoking. Thus, apocynin blocks the ability of cigarette smoke exposure to induce expression of matrix metalloproteinase-12 in human airway epithelia; this proteinase is known to be a key mediator of proteolytic damage in rodent models of emphysema. Also, in a hamster model of emphysema, induced by intratracheal instillation of lipopolysaccaride, apocynin treatment helps to preserve the activity of secretory leukocyte protease inhibitor, which functions to control lung proteolytic activity; this phenomenon reflects the fact that oxidants can deactivate this key protease inhibitor. (Stolk J et al., Am J Respir Crit Care Med 1994; 150:1628-31; Lavigne M C et al., Biochem Biophys Res Comm 2005; 330:194-203)

Asthma is associated with or linked to an NADPH oxidase activity. Activation of NADPH oxidase plays a mediating role in many phases of asthmatic inflammation: activation of mast cells (enabling secretion of histamine and production of leukotrienes), VCAM-mediated migration of eosinophils into lung tissue, pro-inflammatory activity of eosinophils and neutrophils, and the hyperproliferation of airway smooth muscle cells that contributes to lung remodeling in chronic asthma. The ability of ozone exposure to boost bronchoconstrictive responses in asthma patients is largely ameliorated by inhalation of apocynin. In a patient with severe chronic asthma, a temporary substantial improvement in symptoms was noted when serum bilirubin levels increased due to acute hepatitis B; lung function deteriorated again when bilirubin levels returned to normal. (Hoidal J R et al., Antiox Redox Signal 2003; 5:751-8; Brar S S et al., Am J Physiol Lung Cell Mol Physiol 2002; 282:L782-95; Peters E A et al., Free Radic Biol Med 2001; 31:1442-7; Taille C et al., J Biol Chem 2003; 278:27160-8; Caramori G et al., Thorax 2004; 59:170-3; Ohrui et al., Tohoku J Exp Med 2003; 199:193-6)

Allergy is associated with or linked to an NADPH oxidase activity. Antigen-provoked release of histamine and leukotrienes from mast cells—a central feature of allergic syndromes—is contingent on a signaling pathway in which NADPH oxidase activation plays an obligate role, enabling an acute increase in intracellular free calcium. Thus, the NADPH oxidase inhibitor DPI blocks histamine and leukotriene release by mast cells exposed to antigens. (Suzuki Y et al., Chem Immunol Allergy 2005; 87:32-42; Yoshimaru T et al., Clin Exp Allergy 2002; 32:612-8; Suzuki Y et al., J Immunol 2003; 171:6119-27)

Osteoporosis is associated with or linked to an NADPH oxidase activity. Osteoclasts, the bone cells which mediate bone resorption, are modified macrophages with a high capacity to generate oxidants via NADPH oxidase. Inhibitors of NADPH oxidase have been shown to inhibit bone resorption in vitro in bone explants, apparently because hydrogen peroxide is a mediator of the signal transduction required for bone resorption. In ovariectomized mice, infusion of pegylated catalase (which has a prolonged half-life) has been shown to counteract bone resorption, suggesting a key for hydrogen peroxide in the mediation of post-menopausal bone loss. NADPH-derived oxidants also appear to play a role in osteoclast differentiation. (Darden A G et al., J Bone Miner Res 1996; 11:671-5; Yang S et al., J Cell Biochem 2004; 92:238-48; Steinbeck M J et al., J Cell Physiol 1998; 176:574-87; Bax B E et al., Biochem Biophys Res Comm 1992; 183:1153-8; Lean J M et al., Endocrinology 2005; 146:728-35)

Osteoarthritis is associated with or linked to an NADPH oxidase activity. Osteoarthritis is a low-grade inflammatory condition in which certain cytokines—most notably interleukin-1—perturb chondrocyte function, blocking synthesis of matrix proteoglycans while promoting the proteolytic degradation of matrix. Studies with cultured chondrocytes reveal that NADPH-derived oxidants are key mediators of these effects of interleukin-1 on chondrocytes. Peroxynitrite, formed by the spontaneous reaction of superoxide and nitric oxide, suppresses proteoglycan synthesis while promoting apoptosis in interleukin-1-treated chondrocytes; oxidative stress promotes peroxynitrite production directly, and also by aiding induction of the inducible isoform of nitric oxide synthase. (Biemond P, et al., Ann Rheum Dis 1986; 45:249-55; Lo Y Y et al., J Cell Biochem 1998; 69:19-29; Mendes A F et al., J Cell Biochem 2003; 88:783-93; Jouzeau J Y et al., Biorheology 2002; 39:201-14; Oh M et al., J Rheumatol 1998; 25:2169-74)

Gastric Ulcer is associated with or linked to an NADPH oxidase activity. Neutrophil-derived oxidants—dependent on NADPH oxidase activity—are key mediators of the gastric ulceration induced by NSAID drugs. Thus, pre-treatment with superoxide dismutase protects rodents from indomethacin-induced damage to gastric mucosa. Whether NADPH oxidase overactivation in inflammatory cells or gastric mucosal cells might contribute to risk of gastric ulcer or gastric cancer during chronic infection with *H. pylori* is a matter of ongoing investigation. (Vanaanen P M et al., Am J Physiol 1991; 261:G470-5; Park S, et al., Antiox Redox Signal 2004; 6:549-60)

Septic Shock is associated with or linked to an NADPH oxidase activity. Endotoxin-induced shock, culminating in severe hypotension and death, is considerable ameliorated in Gunn rats (a genetic variant with constitutively high plasma bilirubin levels), in rats receiving sustained bilirubin infusions, and in mice pre-treated with oral phycocyanin. These findings are all consistent with a key role for NADPH oxidase activation in septic shock. Indeed, there is evidence that induced oxidant stress is crucial for vascular induction of the inducible nitric oxide synthase, the overactivity of which leads to circulatory collapse. In a rabbit model of endotoxin exposure, concurrent treatment with apocynin has been shown to prevent various types of histological aberrations. (Lanone S et al., FASEB J 2005; 19:1890-2; Wang W W et al., Hepatology 2004; 40:424-33; Kadl A et al., FASEB J 2005: 19:685.19; Lomnitzki L et al., Toxicol Pathol 2000; 28:580-7)

Pulmonary Fibrosis is associated with or linked to an NADPH oxidase activity. Transforming growth factor-beta activity plays a key mediating role in fibrotic syndromes, and, as noted above, NADPH oxidase activation is a mediator of TGF-beta signal transduction. Thus, it is not surprising that bilirubin administration or induction of heme oxygenase-1 (which promotes intracellular bilirubin generation) has been shown to suppress bleomycin-induced pulmonary fibrosis in rodents. Furthermore, bleomycin has reduced capacity to induce pulmonary fibrosis in mice genetically deficient in NADPH oxidase activity. A case report has appeared of resolution of idiopathic pulmonary fibrosis in a patient whose serum bilirubin levels became chronically elevated owing to biliary tract obstruction. (Manoury B et al., Respir Res 2005; 6:11; Thannickal V J et al., J Biol Chem 1995; 270:30334-8; Wang H D et al., Am J Respir Crit Care Med 2002; 165:406-11; Morse D, Am J Respir Cell Mol Biol 2003; 29:S82-6; Ohrui T et al., Tohoku J Exp Med 2001; 193:245-9)

Hepatic Fibrosis is associated with or linked to an NADPH oxidase activity. Hepatic fibrosis reflects hepatotoxin-mediated activation of hepatic stellate cells, resulting in their proliferation and transformation to myofibroblasts that secrete collagen. Oxidant production by NADPH oxidase plays an obligate role in stellate cell activation, and also promotes proliferation of these cells. Induction of hepatic fibrosis is suppressed in mice that are genetically deficient in NADPH oxidase, and inducers of heme oxygenase-1 inhibit the proliferation and collagen synthesis of human myofibroblasts in vitro. (Adachi T et al., Hepatology 2005; 41:1272-81; Bateller R et al., J Clin Invest 2003; 112:1383-94; Li L et al., Gastroenterology 2003; 125:460-9)

Parkinson's Disease is associated with or linked to an NADPH oxidase activity. Peroxynitrite produced by activated microglial cells is a key mediator of the neuronal death and dysfunction associated with chronic neurodegenerative conditions such as Parkinson's or Alzheimer's diseases. Superoxide produced by activated NADPH oxidase reacts with nitric oxide to generate this peroxynitrite. In rodents, MTPT or rotenone-induced neural injury is viewed as a model for human Parkinson's disease; in vitro, co-culture with microglia exacerbates MPTP or rotenone-induced neuronal injury; concurrent exposure to the NADPH oxidase inhibitors apocynin or DPI reverses this effect. Moreover, there is a recent report that feeding spirulina to mice, prior to and following MTPT administration, partially protects striatal dopaminergic neurons from this toxin. This study is of particular interest because it suggests that orally administered phycocyanobilin (PCB) can pass through the blood-brain barrier, inhibiting the NADPH oxidase activity of brain microglia. (Tieu K et al., IUBMB Life 2003; 55:329-35; Gao H M et al., FASEB J 2003; 17:1954-6; Mander P et al., J Neuroinflammation 2005; 2:20; Gao H M et al., J Neurochem 2002; 81:1285-97; Gao H M et al, J Neurosci 2003; 23:181-7; Chamorro G et al., Nutr Neurosci 2006; 9:207-12)

Alzheimer's Disease is associated with or linked to an NADPH oxidase activity. Amyloid beta, believed to be the key mediator of neuronal degeneration in Alzheimer's disease, can activate NADPH oxidase in microglia. Moreover, histological studies demonstrate that microglial NADPH oxidase is activated in this disorder. In neuronal cell cultures, amyloid beta is capable of killing neurons directly; this phenomenon is associated with NADPH oxidase activation in neurons, and antisense inhibition of this activity prevents neuronal death. Thus, there is reason to suspect that NADPH-derived oxidants, produced both in microglia and in neurons, may contribute to neuronal degeneration in Alzheimer's disease. (Zekry D et al., IUBMB Life 2003; 55:307-13; Shimohama S et al., Biochem Biophys Res Comm 2000; 273:5-9; Mander P et al., J Neuroinflammation 2005; 2:20; Jana A et al., J Biol Chem 2004; 279:51451-9)

UV-Mediated Skin Damage is associated with or linked to an NADPH oxidase activity. The skin photo-aging associated with excessive sun exposure reflects uv-mediated effects on epidermal keratinocytes that result in keratinocyte and melanocyte hyperproliferation, accompanied by alterations of the dermal ground substance (collagen degradation, elastin accumulation). This alteration of keratinocyte behavior is in turn contingent on a uv-triggered increase in keratinocyte oxidative stress that is now known to be mediated by activation of NADPH oxidase. This increase in oxidative stress is also likely to contribute to mutagenic alterations in DNA that can give rise to skin cancer (although uv can also mutate DNA more directly by inducing thymine dimer formation). Accordingly, measures which suppress NAPDH oxidase activity also slow the photo-aging process, provide protection from sunburn, and reduce risk for skin cancers. (Beak S M et al., Biochimie 2004; 86:425-9; Wang H et al., Free Radical Biol Med 2005; 38:890-7)

Cancer is associated with or linked to an NADPH oxidase activity. NADPH oxidase activity has been identified in many cancers, and in some cancers, chronic or stimulated NADPH oxidase activity boosts growth factor signaling; in part, this reflects the ability of oxidants to inhibit tyrosine phosphatase enzymes which oppose the activity of tyrosine kinase growth factor receptors. The resulting increase in growth factor activity not only promotes increased cancer proliferation, but also renders cancers relatively resistant to apoptosis and boosts their production of angiogenic factors.

Moreover, activation of NADPH oxidase in endothelial cells occurs during the angiogenic process; this up-regulates the impact of certain angiogenic growth factors, such as VEGF, and contributes more specifically to endothelial tube formation. And there is recent evidence that activation of NADPH oxidase in muscle fibers is a mediator of the loss of skeletal muscle mass associated with cancer cachexia. Hence, inhibition of NADPH oxidase can slow the growth and spread of certain cancers, impede the angiogenic process which supports their spread, and help to prevent cachectic loss of muscle mass.

Such inhibition also has potential for cancer prevention. The increased risk for certain cancers associated with chronic inflammation may reflect, in part, oxidant-mediated mutagenesis; peroxynitrite in particular has notable mutagenic activity. NADPH oxidase is the chief source of oxidants in activated leukocytes, so its inhibition may reduce mutagenesis in inflamed tissues. Also, chronic oxidative stress may play a promotional role in cancer induction by amplifying growth factor activities. (Kim H W et al., Carcinogenesis 2003; 24:235-41; Ohshima H et al., Arch Biochem Biophys 2003; 417:3-11; Teufelhofer O et al., Carcinogenesis 2005; 26:319-29; Brar S S et al., Protoplasma 2003; 221:117-27; Szanto I et al., J Pathol 2005; 207:64-76; Vaquero E C et al., J Biol Chem 2004; 279:34643-54; Brar S S et al., Am J Physiol Cell Physiol 2003; 285:C353-69; Lim S D et al., 2005; 62:200-7; Brar S S et al., Am J Physiol Cell Physiol 2002; 282:C1212-24; Dong J M et al., Free Radic Res 2004; 38:629-379)

Rheumatoid Arthritis is associated with or linked to an NADPH oxidase activity. NADPH oxidase activity is increased in neutrophils obtained from the synovial fluid of patients with rheumatoid arthritis and the related condition spondylarthropathy. It is reasonable to suspect that this oxidative stress contributes to the inflammatory process in the synovium. In mice, apocynin administration is protective in the zymosan-induced arthritis; in particular, it prevents degradation of joint cartilage. Apocynin also lessens joint swelling in collagen-induced arthritis in rats. Analogously, oral administration of spirulina has shown protection in zymosan- and adjuvant-induced arthritis in mice—an effect likely reflecting inhibition of NADPH oxidase by PCB. However, several mutations in mice which negatively impact neutrophil NADPH oxidase activity are associated with increased severity of certain types of induced arthritis. Thus, NADPH oxidase inhibition has complex and countervailing effects on the arthritic process, and will require clinical evaluation before confident predictions can be made. (El Benna J et al., Inflammation 2002; 26:273-8; Hougee S et al. Eur J Pharmacol 2006; 531:264-9; 't Hart B A et al., Free Radic Biol Med 1990; 9:127-31; Lafeber F P et al., Rheumatology 1999; 38:1088-93; Remirez D, et al., Mediators Inflamm 2002; 11:75-9; Rasool M, et al., Biol Pharm Bull 2006; 29:2483-7; Hultqvist M et al., J Immunol 2007; 179:1431-7)

Ulcerative Colitis is associated with or linked to an NADPH oxidase activity. Lymphocytes derived from mucosal lesions in patients with ulcerative colitis or Crohn's disease have elevated NADPH oxidase activity. This activity is also found in colon epithelial cells, and of course in other leukocytes that infiltrate these lesions. Several research groups have disclosed that oxidant stress is a key mediator of tissue damage in inflammatory bowel disease; NADPH oxidase is the most likely source of this oxidant stress. Colitis induced in mice with oral dextran sodium sulfate, is substantially ameliorated by concurrent administration of a heme oxygenase-1 inducer or of biliverdin. (Szanto I et al., J Pathol 2005; 207:164-76; Otamiri T et al., Dig Dis 1991; 9:133-41; Berberat P O, et al., Inflamm Bowel Dis 2005; 11:350-9)

Scleroderma is associated with or linked to an NADPH oxidase activity. Fibroblasts derived from scleroderma lesions produce more oxidant stress than fibroblasts from healthy skin, and NADPH oxidase has been identified as the source of this oxidant stress. Moreover, inhibition of this oxidant stress suppresses the proliferation of scleroderma fibroblasts in vitro, and also reduces their production of collagen. These considerations teach that NAPDH oxidase activation in skin fibroblasts may be an important mediator of the fibroblast hyperproliferation and excessive collagen production characteristic of sclerodermal skin lesions. (Sambo P et al., Arthritis Rheum 2001; 44:2653-64)

Pathological Angiogenesis is associated with or linked to an NADPH oxidase activity. Stimulated angiogenesis plays a pathogenic role in certain disorders, including cancer, macular degeneration, rheumatoid arthritis, and diabetic retinopathy. As noted above, activation of NAPDH oxidase in endothelial cells participating in the process of neovascularization boosts the responsiveness to these cells to certain key growth factors, while contributing to endothelial cell migration and tube formation. Thus, inhibition of NADPH oxidase activity slows the angiogenic process. (Ushio-Fukai M et al., Mol Cell Biochem 2004; 264:85-97; Abid M R et al., FEBS Lett 2000; 486:252-6)

Transplant Rejection is associated with or linked to an NADPH oxidase activity. Recent studies show that administration of heme oxygenase-1 inducers, or of biliverdin, helps to prevent the rejection of cardiac or renal allografts in rats, and also ameliorates the ischemia-reperfusion damage that often afflicts transplanted organs. Thus, inhibition of NADPH oxidase has potential in transplant medicine. (Yamashita K et al., FASEB J 2004; 18:765-7; Bach F H, Hum Immunol 2006; 67:430-2; Nakao A et al., Am J Transplant 2005; 5:282-91)

Chronic Pain Syndrome/Hyperalgesia is associated with or linked to an NADPH oxidase activity. A chronic elevation of superoxide production in sensory neurons has been found to be a key mediator of the hyperalgesia that often accompanies chronic inflammation. Thus, drugs which potently dismutate superoxide have been shown to prevent induction of hyperalgesic syndromes in rats. Although the source of this excess oxidant stress has not yet been definitively identified, NADPH oxidase is expressed in neurons and is likely a key source of the oxidant stress that mediates hyperalgesia. (Chung J M, Mol Intery 2004; 4:248-50; Wang Z Q et al., J Pharmacol Exp Ther 2004; 309:869-78; Kim H K et al, Pain 2004; 111:116-24)

What is claimed is:

1. A phycochemical composition for administration to a mammalian subject, phycochemical composition having a prodrug activity for inhibiting NADPH oxidase activity, the phycochemical composition comprising:
   an isolated phycobilin dissolved or suspended within a pharmaceutically acceptable carrier and
   a capsule having a gelatinous case for containing said isolated phycobilin,
   said isolated phycobilin being converted to a phycorubin when administered to said mammalian subject for inhibiting NADPH oxidase activity,
   said isolated phycobilin being selected from the group consisting of phycocyanobilin, phycoerythrobilin, and phytochromobilin, said phycobilin including a peptide fragment of a phycocyanin conjugated thereto to form a peptide conjugated phycobilin, the peptide fragment being 100 amino acids in length or less, the peptide conjugated phycobilin being substantially purified.

2. A phycochemical composition according to claim 1 wherein said isolated phycobilin is selected from the group consisting of phycocyanobilin, phycoerythrobilin, phytochromobilin, each phycobilin optionally including a peptide fragment of a phycocyanin conjugated thereto.

3. A phycochemical composition according to claim 1 wherein said pharmaceutically acceptable carrier is dry and said capsule is optionally a hard gel.

4. A phycochemical composition according to claim 1 wherein said pharmaceutically acceptable carrier is liquid and said capsule is optionally soft.

5. A phycochemical composition according to claim 3, further comprising one or more ingredient selected from the group consisting of: folic acid, L-arginine, policosanol, soy isoflavone, green tea extract, taurine, coenzyme Q10, potassium salt, magnesium, fish oil, vitamin C, selenium, lutein, zeathanthin, zinc, benfotiamine, and pyridoxamine.

6. A phycochemical composition for administration to a mammalian subject, the phycochemical composition having a prodrug activity for inhibiting NADPH oxidase activity, the phycochemical composition comprising:
   an isolated phycobilin admixed with a pharmaceutically acceptable carrier material or a food grade filler and compressed into a tablet, said isolated phycobilin being converted to a phycorubin when administered to said mammalian subject for inhibiting NADPH oxidase activity,
   said isolated phycobilin being selected from the group consisting of phycocyanobilin, phycoerythrobilin, phytochromobilin, said phycobilin including a peptide fragment of a phycocyanin conjugated thereto to form a peptide conjugated phycobilin, the peptide fragment being 100 amino acids in length or less, the peptide conjugated phycobilin being substantially purified.

7. A phycochemical composition according to claim 6 wherein said isolated phycobilin is selected from the group consisting of phycocyanobilin, phycoerythrobilin, phytochromobilin, each phycobilin optionally including a peptide fragment of a phycocyanin conjugated thereto.

8. A phycochemical composition according to claim 7, further comprising one or more ingredient selected from the group consisting of: folic acid, L-arginine, policosanol, soy isoflavone, green tea extract, taurine, coenzyme Q10, potassium salt, magnesium, fish oil, vitamin C, selenium, lutein, zeathanthin, zinc, benfotiamine, and pyridoxamine.

9. A phycochemical composition for intravenous administration or administration by injection to a mammalian subject, the phycochemical composition having a prodrug activity for inhibiting NADPH oxidase activity, the phycochemical composition comprising:
   an isolated phycobilin dissolved or suspended within a physiologically acceptable sterile solution suitable for injection, said isolated phycobilin being converted to a phycorubin when administered to said mammalian subject for inhibiting NADPH oxidase activity,
   said isolated phycobilin being selected from the group consisting of phycocyanobilin, phycoerythrobilin, phytochromobilin, said phycobilin including a peptide fragment of a phycocyanin conjugated thereto to form a peptide conjugated phycobilin, the peptide fragment being 100 amino acids in length or less, the peptide conjugated phycobilin being substantially purified.

10. A phycochemical composition according to claim 9 wherein said isolated phycobilin is selected from the group consisting of phycocyanobilin, phycoerythrobilin, phytochromobilin, each phycobilin optionally including a peptide fragment of a phycocyanin conjugated thereto.

11. A phycochemical composition for topical administration to a mammalian subject, the phycochemical composition having a prodrug activity for inhibiting NADPH oxidase activity, the phycochemical composition comprising:
   an isolated phycobilin dissolved or suspended within a dermatologically acceptable emollient carrier, said isolated phycobilin being converted to a phycorubin when topically administered to said mammalian subject for inhibiting NADPH oxidase activity,
   said isolated phycobilin being selected from the group consisting of phycocyanobilin, phycoerythrobilin, phytochromobilin, each said phycobilin including a peptide fragment of a phycocyanin conjugated thereto to form a peptide conjugated phycobilin, the peptide fragment being 100 amino acids in length or less, the peptide conjugated phycobilin being substantially purified.

12. A phytochemical composition according to claim 11 wherein said isolated phycobilin is selected from the group consisting of phycocyanobilin, phycoerythrobilin, phytochromobilin, each phycobilin optionally including a peptide fragment of a phycocyanin conjugated thereto.

13. A phycochemical composition according to claim 11 wherein said isolated phycobilin additionally serves as a sunscreen.

14. A nutraceutical composition comprising a nutrient substance admixed with a phycochemical composition comprising an isolated phycobilin,
   said isolated phycobilin being selected from the group consisting of phycocyanobilin, phycoerythrobilin, phytochromobilin, said phycobilin including a peptide fragment of a phycocyanin conjugated thereto to form a peptide conjugated phycobilin, the peptide fragment being 100 amino acids in length or less, the peptide conjugated phycobilin being substantially purified.

15. A nutriceutical composition according to claim 14 wherein said isolated phycobilin is selected from the group consisting of phycocyanobilin, phycoerythrobilin, phytochromobilin, each phycobilin optionally including a peptide fragment of a phycocyanin conjugated thereto.

16. A cosmeceutical composition comprising a cosmetic substance admixed with a phycochemical composition comprising an isolated phycobilin,
   said isolated phycobilin being selected from the group consisting of phycocyanobilin, phycoerythrobilin, phytochromobilin, said phycobilin including a peptide fragment of a phycocyanin conjugated thereto to form a peptide conjugated phycobilin, the peptide fragment being 100 amino acids in length or less, the peptide conjugated phycobilin being substantially purified.

17. A cosmeceutical composition according to claim 16 wherein said isolated phycobilin is selected from the group consisting of phycocyanobilin, phycoerythrobilin, phytochromobilin, each phycobilin optionally including a peptide fragment of a phycocyanin conjugated thereto.

18. A method for prophylaxis or treatment of a subject for a medical condition associated with or linked to an NADPH oxidase activity, the method comprising the step of administering one or more isolated phycobilins to a subject in a prophylactically or therapeutically effective amount for prophylaxis or treatment of a medical condition associated with or linked to an NADPH oxidase activity,
   said isolated phycobilin being selected from the group consisting of phycocyanobilin, phycoerythrobilin, phytochromobilin, said phycobilin including a peptide fragment of a phycocyanin conjugated thereto to form a peptide conjugated phycobilin, the peptide fragment being 100 amino acids in length or less, the peptide conjugated phycobilin being substantially purified.

19. The method of claim 18, wherein the condition is selected from the group consisting of: ischemic heart disease, myocardial infarction, stroke, peripheral atherosclerosis, cerebrovascular atherosclerosis, left ventricular hypertrophy, congestive heart failure, arterial hypertension, pulmonary hypertension, erectile dysfunction, metabolic syndrome, diabetic retinopathy, diabetic neuropathy, diabetic nephropathy, glomerulosclerosis, pulmonary emphysema, asthma, allergy, osteoporosis, osteoarthritis, gastric ulcer, septic shock, fibrosis, pulmonary fibrosis, hepatic fibrosis, Parkinson's disease, Alzheimer's dementia, UV damage to the skin, cancer, rheumatoid arthritis, ulcerative colitis, scleroderma, pathological angiogenesis, transplant rejection, and chronic pain syndrome/hyperalgesia.

20. The method of claim 18, wherein the phycobilin is selected from the group consisting of phycocyanobilin, phycoerythrobilin, phytochromobilin, each phycobilin optionally including a peptide fragment of a phycocyanin conjugated thereto.

21. The method of claim 18, wherein the phycobilin is administered orally, intravenously, or topically.

22. A phycochemical composition according to claim 1 wherein the peptide fragment being selected from a group consisting of peptide fragments having a length of 75 amino acids or less, peptide fragments having a length of 50 amino acids or less, peptide fragments having a length of 25 amino acids or less, and peptide fragments having a length of 10 amino acids in length or less.

23. A phycochemical composition according to claim 1 wherein the peptide conjugated phycobilin forms at least 25 percent or more of the dry weigh of the phycochemical composition.

24. A phycochemical composition according to claim 23 wherein the dry weigh of the phycochemical composition being selected from a group of dry weighs of the phycochemical composition consisting of at least 50 percent dry weigh, at least 75 percent dry weigh, at least 90 percent dry weigh, at least 95 percent dry weigh, and essentially pure dry weigh.

25. A phycochemical chemical composition according to claim 6 wherein the peptide fragment being selected from a group consisting of peptide fragments having a length of 75 amino acids or less, peptide fragments having a length of 50 amino acids or less, peptide fragments having a length of 25 amino acids or less, and peptide fragments having a length of 10 amino acids in length or less.

26. A phycochemical composition according to claim 6 wherein the peptide conjugated phycobilin forms at least 25 percent or more of the dry weigh of the phycochemical composition.

27. A phycochemical composition according to claim 26 wherein the dry weigh of the phycochemical composition being selected from a group of dry weighs of the phycochemical composition consisting of at least 50 percent dry weigh, at least 75 percent dry weigh, at least 90 percent dry weigh, at least 95 percent dry weigh, and essentially pure dry weigh.

28. A phycochemical composition according to claim 9 wherein the peptide fragment being selected from a group consisting of peptide fragments having a length of 75 amino acids or less, peptide fragments having a length of 50 amino acids or less, peptide fragments having a length of 25 amino acids or less, and peptide fragments having a length of 10 amino acids in length or less.

29. A phycochemical composition according to claim 9 wherein the peptide conjugated phycobilin forms at least 25 percent or more of the dry weigh of the phycochemical composition.

30. A phycochemical composition according to claim 29 wherein the dry weigh of the phycochemical composition being selected from a group of dry weighs consisting of at least 50 percent dry weigh, at least 75 percent dry weigh, at least 90 percent dry weigh, at least 95 percent dry weigh, and essentially pure dry weigh.

* * * * *